US008865127B2

(12) United States Patent
Chang et al.

(10) Patent No.: US 8,865,127 B2
(45) Date of Patent: *Oct. 21, 2014

(54) SIMPLIFIED AND IMPROVED METHOD FOR PREPARING AN ANTIBODY OR AN ANTIBODY FRAGMENT TARGETED IMMUNOLIPOSOME FOR SYSTEMIC ADMINISTRATION OF A THERAPEUTIC OR DIAGNOSTIC AGENT

(75) Inventors: Esther H. Chang, Potomac, MD (US); Kathleen F. Pirollo, Rockville, MD (US)

(73) Assignee: Georgetown University, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/820,800

(22) Filed: Jun. 22, 2010

(65) Prior Publication Data

US 2010/0329981 A1    Dec. 30, 2010

Related U.S. Application Data

(60) Division of application No. 10/113,927, filed on Apr. 2, 2002, now Pat. No. 7,780,882, and a continuation-in-part of application No. 09/914,046, filed as application No. PCT/US00/04392 on Feb. 22, 2000, now Pat. No. 7,479,276.

(60) Provisional application No. 60/280,134, filed on Apr. 2, 2001, provisional application No. 60/121,133, filed on Feb. 22, 1999.

(51) Int. Cl.
| | | |
|---|---|---|
| *A61K 49/00* | (2006.01) | |
| *A61K 9/127* | (2006.01) | |
| *A61K 39/00* | (2006.01) | |
| *A61K 39/385* | (2006.01) | |
| *C12N 15/88* | (2006.01) | |
| *C07H 21/04* | (2006.01) | |

(52) U.S. Cl.
CPC .............. *A61K 9/1272* (2013.01); *C12N 15/88* (2013.01); *C12N 2810/40* (2013.01)
USPC ....... 424/9.1; 424/178.1; 424/193.1; 424/450

(58) Field of Classification Search
None
See application file for complete search history.

(56) References Cited

U.S. PATENT DOCUMENTS

| | | | |
|---|---|---|---|
| 4,946,778 A | 8/1990 | Ladner et al. | |
| 5,688,488 A | 11/1997 | Low et al. | |
| 5,786,214 A | 7/1998 | Holmberg | |
| 5,977,322 A | 11/1999 | Marks et al. | |
| 6,071,533 A | 6/2000 | Papahadjopoulos et al. | |
| 6,099,842 A | 8/2000 | Pastan et al. | |
| 6,200,956 B1 | 3/2001 | Scherman et al. | |
| 6,210,707 B1 | 4/2001 | Papahadjopoulos et al. | |
| 6,693,086 B1 | 2/2004 | Dow et al. | |
| 6,794,128 B2 | 9/2004 | Marks et al. | |
| 7,022,336 B2 | 4/2006 | Papahadjopoulos et al. | |
| 7,741,300 B2 | 6/2010 | Dow et al. | |
| 2001/0008759 A1 | 7/2001 | Marks et al. | |
| 2003/0044407 A1 | 3/2003 | Chang et al. | |
| 2004/0209366 A1 | 10/2004 | Papahadjopoulos et al. | |

FOREIGN PATENT DOCUMENTS

| | | |
|---|---|---|
| EP | 0 451 972 | 10/1991 |
| JP | 09-110722 | 4/1997 |
| WO | WO 83/02069 A1 | 6/1983 |
| WO | WO 95/14380 A1 | 6/1995 |
| WO | WO 95/35301 A1 | 12/1995 |
| WO | WO 97/28817 | 8/1997 |
| WO | WO 98/20857 A1 | 5/1998 |
| WO | WO 99/25320 A1 | 5/1999 |
| WO | WO 99/59643 A2 | 11/1999 |
| WO | WO 00/15649 A1 | 3/2000 |
| WO | WO 00/50008 A2 | 8/2000 |

OTHER PUBLICATIONS

Aigner, Journal of Biomedicine and Biotechnology, vol. 2006, pp. 1-15, 2006.
Allen, T. M., et al.: "A New Strategy for Attachment of Antibodies to Sterically Stabilized Liposomes Resulting in Efficient Targeting to Cancer Cells", Biochimica et Biophysica Acta, vol. 1237, pp. 99-108-, 1995.
Allen, T. M., et al.: "Antibody-Targeted Stealth® Liposomes" in Stealth Liposomes, pp. 233-244, 1995.
Aoki, K., et al.: Liposome-Mediated In Vivo Gene Transfer of Antisense K-ras Construct Inhibits Pancreatic Tumor Dissemination in the Murine Peritoneal Cavity, Cancer Research, vol. 55, pp. 3810-3816, 1995.

(Continued)

*Primary Examiner* — Gerald R Ewoldt
*Assistant Examiner* — Marianne Dibrino
(74) *Attorney, Agent, or Firm* — Fanelli Haag & Kilger PLLC

(57) ABSTRACT

Provided herein is an antibody- or antibody fragment-targeted cationic immunoliposome complex prepared by a method comprising the steps of (a) preparing an antibody or antibody fragment; (b) mixing the antibody or antibody fragment with a cationic liposome and to form a cationic immunoliposome wherein the antibody or antibody fragment is complexed with the cationic liposome, but is not chemically conjugated to the cationic liposome and wherein said antibody or antibody fragment does not comprise a lipid tag; and (c) mixing the cationic immunoliposome with a therapeutic or diagnostic agent to form the antibody- or antibody fragment-targeted cationic immunoliposome. Also provided is an antibody- or antibody fragment-targeted cationic immunoliposome comprising an antibody or antibody fragment; a cationic liposome, wherein the antibody or antibody fragment is complexed with the cationic liposome, but is not chemically conjugated to the cationic liposome and wherein said antibody or antibody fragment does not comprise a lipid tag and a therapeutic or diagnostic agent.

70 Claims, 16 Drawing Sheets

(56) References Cited

OTHER PUBLICATIONS

Bajoria, R., et al.: "Effect of Surface Charge of Small Unilamellar Liposomes on Uptake and Transfer of Carboxyfluorescein Across the Perfused Human Term Placenta [Regular Articles]," Pediatric Research, vol. 42, pp. 520-527, 1997.
Bajoria, R., et al.: "Endocytotic Uptake of Small Unilamellar Liposomes by Human Trophoblast Cells in Culture", Human Reproduction, vol. 12, pp. 1343-1348, 1997.
Bauer, K. S., et al.: "Inhibition of Angiogenesis by Thalidomide Requires Metabolic Activation, Which is Species-Dependent," Biochemical Pharmacology, vol. 55, pp. 1827-1834, 1998.
Bristow, R. G., et al.: "The p53 Gene As a Modifier of Intrinsic Radiosensitivity: Implications for Radiotherapy," Radiotherapy and Oncology, vol. 40, pp. 197-223, 1996.
Capitosti, S. M., et al.: "Thalidomide Analogues Demonstrate Dual Inhibition of Both Angiogenesis and Prostate Cancer," Bioorganic & Medicinal Chemistry, vol. 12, pp. 327-336, 2004.
Chackal-Roy, M., et al.: "Stimulation of Human Prostatic Carcinoma Cell Growth by Factors Present in Human Bone Marrow," The Journal of Clinical Investigation, vol. 84, pp. 43-50, 1989.
Chen, L., et al.: "Synergistic Activation of p53 by Inhibition of MDM2 Expression and DNA Damage," Proceedings of the National Academy of Sciences of the United States of America, vol. 95, pp. 195-200, 1998.
Cheng, P.-W., "Receptor Ligand-Facilitated Gene Transfer: Enhancement of Liposome-Mediated Gene Transfer and Expression by Transferrin," Human Gene Therapy, vol. 7, pp. 275-282, 1996.
Chiarugi, V., et al.: "Cox-2, iNOS and p53 As Play-Makers of Tumor Angiogenesis (Review)," International Journal of Molecular Medicine, vol. 2, pp. 715-719, 1998.
Clark, P. R., et al.: "Cationic Lipid-Mediated Gene Transfer: Current Concepts," Current Opinion in Molecular Therapeutics, vol. 1, pp. 158-176, 1999.
Compagnon, et al.: "Enhanced Gene Delivery and Expression in Human Hepatocellular Carcinoma Cells by Cationic Immunoliposomes," Journal of Liposome Research, vol. 7(1), pp. 127-141, 1997.
Cristiano, R. J., et al.: "Strategies to Accomplish Gene Delivery Via the Receptor-Mediated Endocytosis Pathway," Cancer Gene Therapy, vol. 3, pp. 49-57, 1996.
D'Amato, R. J., et al.: "Thalidomide is an Inhibitor of Angiogenesis," Proceedings of the National Academy of Sciences of the United States of America, vo. 91, pp. 4082-4085, 1994.
De Kruif, et al.: "Biosynthetically Lipid-Modified Human scFv Fragments from Phase Display Libraries as Targeting Molecules for Immunoliposomes," FEBS Letters, vol. 399, pp. 232-236, 1996.
Dredge, K., et al.: "Immunological Effects of Thalidomide and Its Chemical and Functional Analogs," Critical Reviews in Immunology, vol. 22, pp. 425-437, 2002.
Dredge, K., et al.: "Novel Thalidomide Analogues Display Anti-Angiogenic Activity Independently of Immunomodulatory Effects," British Journal of Cancer, vol. 87, pp. 1166-1172, 2002.
Drummond, D. C., et al.: "Optimizing Liposomes for Delivery of Chemotherapeutic Agents to Solid Tumors," Pharmacological Review, vol. 51, pp. 691-743, 1999.
Dubé, D., et al.: "Preparation and Tumor Cell Uptake of Poly(N-isopropylacrylamide) Folate Conjugates." Bioconjugate Chemistry, vol. 13, pp. 685-692, 2002.
Elliott, R. L., et al.: "Breast Carcinoma and the Role of Iron Metabolism: A Cytochemical, Tissue Culture, and Ultrastructural Study," Annals of the New York Academy of Sciences, vol. 698, pp. 159-166, 1993.
Felgner, P. L., et al.: Improved Cationic Lipid Formulations for In Vivo Gene Therapy, Annals of the New York Academy of Sciences, vol. 772, pp. 126-139, 1995.
Fernandes-Alnemri, T., et al.: "CPP32, a Novel Human Apoptotic Protein with Homology to *Caenorhabditis elegans* Cell Death Protein Ced-3 and Mammalian Interleukin-1 β-Converting Enzyme," Journal of Biological Chemistry, vol. 269, pp. 30761-30764, 1994.

Forssen, E., et al.: "Ligand-Targeted Liposomes," Advanced Drug Delivery Reviews, vol. 29, pp. 249-271, 1998.
Forsyth, C. J., et al.: "Thalidomide Responsive Chronic Pulmonary GVHD," Bone Marrow Tranplantation, vol. 17, pp. 291-293, 1996.
Fujiwara, T., et al.: "A Retroviral Wild-Type p53 Expression Vector Penetrates Human Lung Cancer Spheroids and Inhibits Growth by Inducing Apoptosis," Cancer Research, vol. 53, pp. 4129-4133, American Association for Cancer Research, 1993.
Fujiwara, T., et al.: "Induction of Chemosensitivity in Human Lung Cancer Cells In Vivo by Adenovirus-Mediated Transfer of the Wild-Type p53 Gene," Cancer Research, vol. 54, pp. 2287-2291, 1994.
Gershon, H., et al.: "Mode of Formation and Structural Features of DNA-Cationic Liposome Complexes Used for Transfection", Biochemistry, vol. 32, pp. 7143-7151, 1993.
Grayhack, J. T., et al.: "Analysis of Specific Proteins in Prostatic Fluid for Detecting Prostatic Malignancy," Journal of Urology, vol. 121, pp. 295-299, 1979.
Hamada, K., et al.: "Adenovirus-Mediated Transfer of a Wild-Type p53 Gene and Induction of Apoptosis in Cervical Cancer," Cancer Research, vol. 56, pp. 3047-3054, 1996.
Hamada, K., et al.: "Growth Inhibition of Human Cervical Cancer Cells with the Recombinant Adenovirus p53 In Vitro," Gynecological Oncology, vol. 60, pp. 373-379, 1996.
Hamada, K., et al.: "Adenovirus-Mediated Transfer of HPV 16 E6/E7 Antisense RNA to Human Cervical Cancer Cells," Gynecological Oncology, vol. 63, pp. 219-227, 1996.
Hamel, E., et al.: "Antitumor 2,3-Ddiydro-2-(aryl)-4(1H)-quinazolinone Derivatives. Interactions with Tubulin," Biochemical Pharmacology, vol. 51, pp. 53-59, 1995.
Heere-Ress, E., et al.: "Thalidomide Enhances the Anti-Tumor Activity of Standard Chemotherapy in a Human Melanoma Xenotransplantation Model," Journal of Investigative Dermatology, vol. 125, pp. 201-206, 2005.
Hour, M.-J., et al.: "6-Alkylamino- and 2,3-Dihydro-3'-methoxy-2-phenyl-4-quinazolinones and Related Compounds: Their Synthesis, Cytotoxicity, and Inhibition of Tubulin Polymerization," Journal of Medicinal Chemistry, vol. 43, pp. 4479-4487, 2000.
Huwyler, J., et al.: "Brain Drug Delivery of Small Molecules Using lmmunoliposomes," Proceedings of the National Academy of Sciences of the United States of America, vol. 93, pp. 14164-14169, 1996.
Jacobson, J. M., et al.: "Thalidomide for the Treatment of Oral Aphthous Ulcers in Patients with Human Immunodeficiency Virus Infection," New England Journal of Medicine, vol. 336, pp. 1487-1493, 1997.
Jiang, et al.: "Cell-Type-Specific Gene Transfer into Human Cells with Retroviral Vectors that Display Single-Chain Antibodies," Journal of Virology, vol. 72(12), pp. 10148-10156, 1998.
Johnson, P., et al.: "Expression of Wild-Type p53 Is Not Compatible with Continued Growth of p53-Negative Tumor Cells," Molecular Cell Biology, vol. 11, pp. 1-11, 1991.
Kerr, J. F. R., et al.: "Apoptosis: Its Significance in Cancer and Cancer Therapy," Cancer, vol. 73, pp. 2013-2026, 1994.
Keer, H. N., et al.: "Elevated Transferrin Receptor Content in Human Prostate Cancer Cell Lines assessed In Vitro and In Vivo," Journal of Urology, vol. 143, pp. 381-385, 1990.
Kenyon, B. M., et al.: "Effects of Thalidomide and Related Metabolites in a Mouse Corneal Model of Neovascularization," Experimental Eye Research, vol. 64, pp. 971-978, 1997.
Kirpotin, D., et al.: "Sterically Stabilized Anti-HER2 Immunoliposomes: Design and Targeting to Human Breast Cancer Cells in Vitro," Biochemistry, vol. 36, pp. 66-75, 1997.
Kobatake, et al.: "A Fluoroimmunoassay Based on Immunoliposomes Containing Genetically Engineered Lipid-Tagged Antibody," Analytical Chemistry, vol. 69, pp. 1295-1298, 1997.
Koning, G. A., et al.: "Antiproliferatiave Effect of Immunoliposomes Containing 5-Fluorodeoxyuridine-Dipalmitate on Colon Cancer Cells," British Journal of Cancer, vol. 80, pp. 1718-1725, 1999.
Koning, G. A., et al.: "Selective Transfer of a Lipophilic Progdrug of 5-Fluorodeoxyuridine from Immunoliposomes to Colon Cancer Cells," Biochimica et Biophysica Acta, vo. 1420, pp. 153-167, 1999.

(56) References Cited

OTHER PUBLICATIONS

Konishi, H., et al.: "Targeting Strategy for Gene Delivery to Carcinoembryonic Antigen-Producing Cancer Cells by Retrovirus Displaying a Single-Chain Variable Fragment Antibody," Human Gene Therapy, vol. 9, pp. 235-248, 1998.

Lasic, D. D., et al.: "Sterically Stabilized Liposomes in Cancer Therapy and Gene Delivery," Current Opinion in Molecular Therapeutics, vol. 1, pp. 177-185, 1999.

Lasic, D. D., et al.: "Liposomes Revisited," Science, vol. 267, pp. 1275-1276, 1995.

Laukkanen, M.-L., et al.: "Functional Immunoliposomes Harboring a Biosynthetically Lipid-Tagged Single-Chain Antibody," Biochemistry, vol. 33, pp. 11664-11670, 1994.

Lee, R. J., et al.: "Folate-Targeted, Anionic Liposome-Entrapped Polylysine-Condensed DNA for Tumor Cell-Specific Gene Transfer," The Journal of Biological Chemistry, vol. 271, pp. 8481-8487, 1996.

Lee, Y. J., et al.: "Docetaxel and Cisplatin as Primary Chemotherapy for Treatment of Locally Advanced Breast Cancers," Clinical Breast Cancer, vol. 5, pp. 371-376, 2004.

Lesoon-Wood, L. A., et al.: "Systemic Gene Therapy with p53 Reduces Growth and Metastases of a Malignant Human Breast Cancer in Nude Mice," Human Gene Therapy, vol. 6, pp. 395-405, 1995.

Lewis, J. G., et al.: "A Serum-Resistant Cytofectin for Cellular Delivery of Antisense Oligodeoxynucleotides and Plasmid DNA," Proceedings of the National Academy of Sciences of the United States of America, vol. 93, pp. 3176-3181, 1996.

Li, S., et al.: "Functional Pleomorphism of Liposomal Gene Delivery Vectors-Lipoplex and Lipopolyplex," Lipsomes-Rational Design, pp. 89-124, 1998.

Lima, L. M., et al.: "Synthesis and Anti-Inflammatory Activity of Phthalimide Derivatives, Designed as New Thalidomide Analogues," Bioorganic & Medicinal Chemistry, vol. 10, pp. 3067-3073, 2002.

Liu, T. J., et al.: "Growth Suppression of Human Head and Neck Cancer Cells by the Introduction of a Wild-Type p53 Gene via a Recombinant Adenovirus," Cancer Research, vol. 54, pp. 3662-3667, 1994.

Lowe, S. W.: "Cancer Therapy and p53," Current Opinion in Oncology, vol. 7, pp. 547-553, 1995.

MacLean, A. L., et al.: "Immunoliposomes as Targeted Delivery Vehicles for Cancer Therapeutics (Review)," The International Journal of Oncology, vol. 11, pp. 325-332, 1997.

Mamot, et al.: "Targeting the Epidermal Growth Factor Receptor (EGFR)—A New Therapeutic Option in Oncology?," Swiss Medical Weekly, vol. 136, pp. 4-12, 2006.

Marinina, J., et al.: "Stabilization of Vinca Alkaloids Encapsulated in Poly(lactide-co-glycolide) Microspheres," Pharmaceutical Research, vol. 17, pp. 677-683, 2000.

Martin, et al.,: "Irreversible Coupling of Immunoglobulin Fragments to Performed Vesicles. An Improved Method for Liposome Targeting," The Journal of Biological Chemistry, vol. 257(1), pp. 286-288, 1982.

Martin, F. et al.: "Retroviral Vector Targeting to Melanoma Cells by Single-Chain Antibody Incorporation in Envelope," Human Gene Therapy, vol. 9, pp. 737-746, 1998.

Massing, U.: "Cancer Therapy with Liposomal Formulations of Anticancer Drugs," The International Journal of Clinical Pharmacology and Therapeutics, vol. 35, pp. 87-90, 1997.

Mastrobattista, E., et al.: "Immunoliposomes for the Targeted Delivery of Antitumor Drugs," Advanced Drug Delivery Reviews, vol. 40, pp. 103-127, 1999.

Matlashewski, G.: "p53: Twenty years on, Meeting Review," Oncogene Review, vol. 18, pp. 7618-7620, 1999.

Mattioli, R., et al.: "Long-Survival in Responding Patients with Metastatic Breast Cancer Treated with Doxorubicin-Docetaxel Combination. A Multicentre Phase II Trial," Anticancer Research, vol. 24, pp. 3257-3262, 2004.

May, P., et al.: "Twenty Years of p53 Research: Structural and Functional Aspects of the p53 Protein," Oncogene Reviews, vol. 18, pp. 7621-7636, 1999.

McCarthy, D. M., et al.: "Thalidomide for the Therapy of Graft-Versus-Host Disease Following Allogeneic Bone Marrow Transplantation," Biomedicine & Pharmacotherapy, vol. 43, pp. 693-697, 1989.

Miller, K. D,, et al.: "Taxanes in the Treatment of Breast Cancer: A Prodigy Comes of Age," Cancer Investigation, vol. 17, pp. 121-136, 1999.

Miyamota, T., et al.: "Transferrin Receptor in Oral Tumors," International Journal of Oral and Maxillofacial Surgery, vol. 23, pp. 430-433, 1994.

Miyashita, T., et al.: "Tumor Suppressor p53 is a Regulator of bcl-2 and bax Gene Expression In Vitro and In Vivo," Oncogene, vol. 9, pp. 1799-1805, 1994.

Morishige, H., et al.: "In Vitro Cytostatic Effect of TNF (Tumor Necrosis Factor) Entrapped in Immunoliposomes on Cells Normally Insensitive to TNF," Biochimica et Biophysica Acta, vol. 1151, pp. 59-68, 1993.

Nag, A., et al.: "A Colorimetric Estimation of Polyethyleneglycol-Conjugated Phospholipid in Stealth Liposomes," Analytical Biochemistry, vol. 250, pp. 35-43, 1997.

Nam, S. M., et al.: "Sterically Stabilized anti-$G_{M3}$, Anti-Le$^x$ Immunoliposomes: Targeting to B16BL6, HRT-18 Cancer Cells," Oncology Research, vol. 11, pp. 9-16, 1999.

Ng, K.-Y., et al.: "The Effects of Polyethyleneglycol (PEG)-Derived Lipid on the Activity of Target-Sensitive Immunoliposome," The International Journal of Pharmacology, vol. 193, pp. 157-166, 2000.

Ng, S. S. W., et al.: "Antiangiogenic Activity of N-Substituted and Tetrafluorinated Thalidomide Analogues," Cancer Research, vol. 63, pp. 3189-3194, 2003.

Nguyen, M., et al.: "Thalidomide and Chemotherapy Combination: Preliminary Results of Preclinical and Clinical Studies," International Journal of Oncology, vol. 10, pp. 965-969, 1997.

Nicholson, D. W., et al.: "Identification and Inhibition of the ICE/CED-3 Protease Necessary for Mammalian Apotosis," Nature, vol. 376, pp. 37-43, 1995.

Nicholson, I. C., et al.: "Construction and Characterization of a Functional CD19 Specific Single Chain Fv Fragment for Immunotherapy of B Lineage Leukaemia and Lymphoma," Molecular Immunology, vol. 34, pp. 1157-1165, 1997.

Nilsson, B., et al.: "Fusion Proteins in Biotechnology and Structural Biology," Current Opinion in Structural Biology, vol. 2, pp. 569-575, 1992.

Pagnan, G., et al.: "GD2-Mediated Melanoma Cell Targeting and Cytotoxicity of Liposome-Entrapped Fenretinide," The International Journal of Cancer, vol. 81, pp. 268-274, 1999.

Park, J. W., et al.: "Development of Anti-p185$^{HER2}$ Immunoliposomes for Cancer Therapy," Proceedings of the National Academy of Sciences of the United States of America, vol. 92, pp. 1327-1331, 1995.

Park, J. W., et al.: "Immunoliposomes for Cancer Treatment," Advances in Pharmacology, vol. 40, pp. 399-435, 1997.

Park, J. W., et al.: "Tumor Targeting Using Anti-Her2 Immunoliposomes," Journal of Controlled Release, vol. 74, pp. 95-113, 2001.

Pirollo, K. F., et al.: "p53 Mediated Sensitization of Squamous Cell Carcinoma of the Head and Neck to Radiotherapy," Oncogene, vol. 14, pp. 1735-1746, 1997.

Pirollo, K. F., et al.: "Immunoliposomes: A Targeted Delivery Tool for Cancer Treatment," Vector Targeting for Therapeutic Gene Delivery, pp. 33-62, 2002.

Poon, R. Y. M.: "Advances in Monoclonal Antibody Applications: Bispecific Antibodies," Biotechnology International: International Developments in the Biotechnology Industry, pp. 113-128, 1997.

Rait, A. S., et al.: "Inhibitory Effects of the Combination of HER-2 Antisense Oligonucleotide and Chemotherapeutic Agents Used for the Treatment of Human Breast Cancer," Cancer Gene Therapy, vol. 8, pp. 728-739, 2001.

Reyes-Terán, G., et al.: Effects of Thalidomide on HIV-Associated Wasting Syndrome: A Randomized, Double-Blind, Placebo-Controlled Clinical Trial, AIDS, vol. 10, pp. 1501-1507, 1996.

Roh, et al.: Her2/neu Antisense Targeting of Human Breast Carcinoma, Oncogene, vol. 19, pp. 6138-6143, 2000.

(56) References Cited

OTHER PUBLICATIONS

Rossi, M. C., et al.: "Selective Stimulation of Prostatic Carcinoma Cell Proliferation by Trandferrin," Proceedings of the National Academy of Sciences of the United States of America, vol. 89, pp. 6197-6201, 1992.

Rowinsky, E. K., et al.: "Paclitaxel (Taxol)," New England Journal of Medicine, vol. 332, pp. 1004-1014, 1995.

Ruley, H. E., et al.: "p53 and Response to Chemotherapy and Radiotherapy," Important Advances in Oncology, pp. 37-56, 1996.

Sachdeva, M. S., et al.: "Drug Targeting Systems for Cancer Chemotherapy," Expert Opinion on Investigational Drugs, vol. 7, pp. 1849-1964, 1998.

Sapra, P., et al.: "Improved Therapeutic Responses in Xenograft Model of Human B Lymphoma (Namalwa) for Liposomal Vincristine versus Liposomal Doxorubicin Targeted via Anti-CD19 IgG2a or Fab' Fragments," Clinical Cancer Research, vol. 10, pp. 1100-1111, 2004.

Schier, R., et al.: "In Vitro and In Vivo Characterization of a Human Anti-c-erbB-2 Single Chain Fv Isolated from a Filamentous Phage Antibody Library," Immunotechnology, vol. 1, pp. 73-81, 1995.

Shahinian, et al.: "A Novel Strategy Affords High-Yield Coupling of Antibody Fab Fragments to Liposomes," Biochimica et Biophysica Act, vol. 1239, pp. 157-167, 1995.

Sidransky, D., et al.: "Clinical Implications of the p53 Gene," Annual Review of Medicine, vol. 47, pp. 285-301, 1996.

Simoes, S. et al.: "Enhancement of Cationic Liposome-Mediated Gene Delivery by Transferrin and Fusogenic Peptides," The 24$^{th}$ International Symposium on Controlled Release of Bioactive Materials, vol. 24, pp. 659-660, 1997.

Spragg, et al.: "Immunotargeting of Liposomes to Activated Vascular Endothelial Cells: A Strategy for Site-Selective Delivery in the Cardiovascular System," Proceedings of the National Academy of Sciences, vol. 94, pp. 8795-8800, 1997.

Srivastava, S., et al.: "Recombinant Adenovirus Vector Expressing Wild-Type p53 is a Potent Inhibitor of Prostate Cancer Cell Proliferation," Urology, vol. 46, pp. 843-848, 1995.

Suzuki, S., et al.: "Modulation of Doxorubicin Resistance in a Doxorubicin-Resistant Human Leukaemia Cell by an Immunoliposome Targeting Transferring Receptor," British Journal of Cancer, vol. 76, pp. 83-89, 1997.

Tewari, M., et al.: "Yama/CPP32β, a Mammalian Homolog of CED-3, Is a CrmA-Inhibitable Protease That Cleaves the Death Susbstrate Poly(ADP-Ribose) Polymerase," Cell, vol. 81, pp. 801-809, 1995.

Thierry, A. R., et al.: "Systemic Gene Therapy: Biodistribution and Long-Term Expression of a Transgene in Mice," Proceedings of the National Academy of Sciences of the United States of America, vol. 92, pp. 9742-9746, 1995.

Thorstensen, K., et al.: "The Transferrin Receptor: Its Diagnostic Value and its Potential as Therapeutic Target," Scandinavian Journal of Clinical and Laboratory Investigation, vol. 53(215), pp. 113-120, 1993.

Tseng, S., et al.: "Rediscovering Thalidomide: A Review of its Mechanism of Action, Side Effects, and Potential Uses," Journal of the American Academy of Dermatology, vol. 35, pp. 969-979, 1996.

Turk, M. J., et al.: "Characterization of a Novel pH-Sensitive Peptide that Enhances Drug Release from Folate-Targeted Liposomes at Endosomal pHs," Biochimica et Biophysica Acta, vol. 1559, pp. 56-68, 2002.

Venugopalan, P., et al.: "pH-Sensitive Liposomes: Mechanism of Triggered Release to Drug and Gene Delivery Prospects," Pharmazie, vol. 57, pp. 659-671, 2002.

Vertut-Doï, A., et al.: "Binding and Uptake of Liposomes Containing a Poly(Ethylene Glycol) Derivative of Cholesterol (Stealth Liposomes) by the Macrophage Cell Line J774: Influence of PEG Content and its Molecular Weight," Biochimica et Biophysica Acta, vol. 1278, pp. 19-28, 1996.

Vogelsang, G. B., et al.: "Treatment and Prevention of Acute Graft-Versus-Host Disease with Thalidomide in a Rat Model," Transplantation, vol. 41, pp. 644-647, 1986.

Volpert, O. V., et al.: "Sequential Development of an Angiogenic Phenotype by Human Fibroblasts Progressing to Tumorigenicity," Oncogene, vol. 14, pp. 1495-1502, 1997.

Wang, D., et al.: "Generation and Characterization of an Anti-CD19 Single-Chain Fv Immunotoxin Composed of C-Terminal Disulfide-Linked dgRTA," Bioconjugate Chemistry, vol. 8, pp. 878-884, 1997.

Weinberg, E. D., et al.: "Roles of Iron in Neoplasia: Promotion, Prevention, and Therapy," Biological Trace Element Research, vol. 34, pp. 123-140, 1992.

Wright, S.E., et al.: "Bilayer Stabilization fo Phosphatidylethanolamine by N-Biotinylphosphatidylethanolamine," Biochimica et Biophysica Acta, vol. 1103, pp. 172-178, 1992.

Xu, et al.: "Systemic Tumor-Targeted Gene Delivery by Anti-Transferrin Receptor scFv-Immunoliposomes," Molecular Cancer Therapeutics, vol. 1, pp. 337-346, 2002.

Xu, et al.: "Transferrin-Liposome-Mediated p53 Sensitization of Squamous Cell Carcinoma of the Head and Neck to Radiation In Vitro," Human Gene Therapy, vol. 8, pp. 467-475, 1997.

Xu, L., et al.: "Self-Assembly of a Virus-Mimicking Nanostructure System for Efficient Tumor-Targeted Gene Delivery," Human Gene Therapy, vol. 13, pp. 469-481, 2002.

Xu, L., et al.: "Systemic p53 Gene Therapy in Combination with Radiation Results in Human Tumor Regression," Tumor Targeting, vol. 4, pp. 92-104, 1999.

Xu, L., et al.: "Systemic p53 Gene Therapy of Cancer with Immunolipoplexes Targeted by Anti-Transferrin Receptor scFv," Molecular Medicine, vol. 7, pp. 723-734, 2001.

Xu, L., et al.: "Transferrin-Liposome-Mediated Systemic p53 Gene Therapy in Combination with Radiation Results in Regression of Human Head and Neck Cancer Xenografts," Human Gene Therapy, vol. 10, pp. 2941-2952, 1999.

Xu, L., et al.: "Tumor-Targeted p53-Gene Therapy Enhances the Efficacy of Conventional Chemo/Radiotherapy," Journal of Controlled Release, vol. 74, pp. 115-128, 2001.

Yang, C., et al.: "Adenovirus-Mediated Wild-Type p53 Expression Induces Apoptosis and Suppresses Tumorigenesis of Prostatic Tumor Cells," Cancer Research, vol. 55, pp. 4210-4213, 1995.

Yazdi, P. T., et al.: "Influence of Cellular Trafficking on Protein Synthesis Inhibition of Immunotoxins Directed Against the Transferrin Receptor," Cancer Research, vol. 55, pp. 3763-3771, 1995.

Yoshida, et al.: "Simple Preparation and Characterization of Cationic Liposomes Associated with a Monoclonal Antibody Against Glioma-Associated Antigen (Immunoliposomes)," Journal of Liposome Research, vol. 5(4), pp. 981-995, 1995.

Yu, D., et al.: "Liposome-Mediated In Vivo E1A Gene Transfer Suppressed Dissemination of Ovarian Cancer Cells That Overexpress HER-2/neu," Oncogene, vol. 11, pp. 1383-1388, 1995.

Yu, W., et al.: "Enhanced Transfection Efficiency of a Systemically Delivered Tumor-Targeting Immunolipoplex by Inclusion of a pH-Sensitive Histidylated Oligolysine Peptide," Nucleic Acids Research 32: e48, 2004.

Zhang, W.-W., et al.: "Advances in Cancer Gene Therapy," Advances in Pharmacology, vol. 32, pp. 289-341, 1995.

Database Medline Accession No. NLM7621238, English language abstract for Zhang, W. W., et al., "High-Efficiency Gene Transfer and High-Level Expression of Wild-Type p53 in Human Lung Cancer Cells Mediated by Recombinant Adenovirus," Cancer Gene Therapy, vol. 1, pp. 5-13, 1994.

Zignani, M., et al.: In Vitro Characterization of a Novel Polymeric-Based pH-Sensitive Liposome System, Biochimica et Biophysica Acta, vol. 1463, pp. 383-394, 2000.

Office Action in related co-pending U.S. Appl. No. 09/914,046 mailed Jul. 26, 2007.

Office Action in related co-pending U.S. Appl. No. 09/914,046 mailed Dec. 6, 2006.

Office Action in related co-pending U.S. Appl. No. 09/914,046 mailed Jun. 9, 2006.

Office Action in related co-pending U.S. Appl. No. 09/914,046 mailed Jul. 28, 2005.

Office Action in related co-pending U.S. Appl. No. 09/914,046 mailed Nov. 29, 2004.

(56) References Cited

OTHER PUBLICATIONS

Office Action in related U.S. Appl. No. 10/113,927, now Patent No. 7,780,882 mailed Sep. 22, 2005.
Office Action in related U.S. Appl. No. 10/113,927, now Patent No. 7.780,882 mailed May 31, 2006.
Office Action in related U.S. Appl. No. 10/113,927, now Patent No. 7,780,882 mailed Dec. 5, 2006.
Office Action in related U.S. Appl. No. 10/113,927, now U.S. Patent No. 7,780,882 mailed Jul. 27, 2007.
Office Action in related U.S. Appl. No. 10/113,927, now U.S. Patent No. 7.780,882 mailed Nov. 6, 2007.
Office Action in related U.S. Appl. No. 10/113,927, now U.S. Patent No. 7,780,882 mailed Feb. 7, 2008.
Office Action in related U.S. Appl. No. 10/113,927, now U.S. Patent No. 7,780,882 mailed Nov. 25, 2008.
Notice of Allowance in related U.S. Appl. No. 10/113,927, now Patent No. 7,780,882 mailed Mar. 23, 2010.
Office Action in related co-pending U.S. Appl. No. 11/520,796 mailed Aug. 3, 2010.
Office Action in related co-pending U.S. Appl. No. 11/798,296 mailed Jan. 14, 2011.
The Journal of Gene Medicine, "Gene-Therapy Clinical Trials Worldwide," available online at: abedia.com/wiley/index.html, 1 page, accessed Sep. 29, 2011.
International Search Report for International Application No. PCT/US07/11407, ISA US, Alexandria, VA, mailed on Oct. 10, 2007.
Office Action in related co-pending U.S. Appl. No. 11/520,796, mailed Apr. 11, 2011, 12 pages.

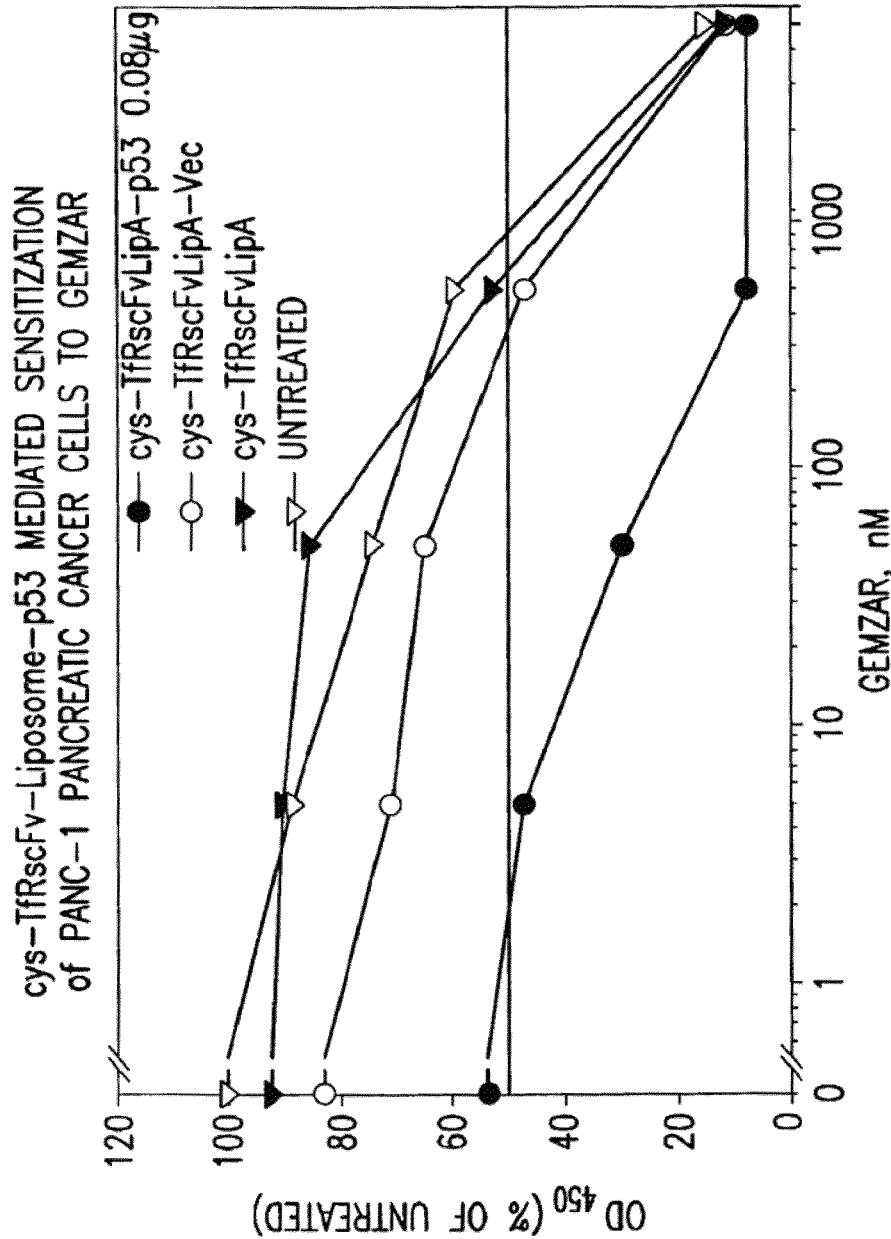

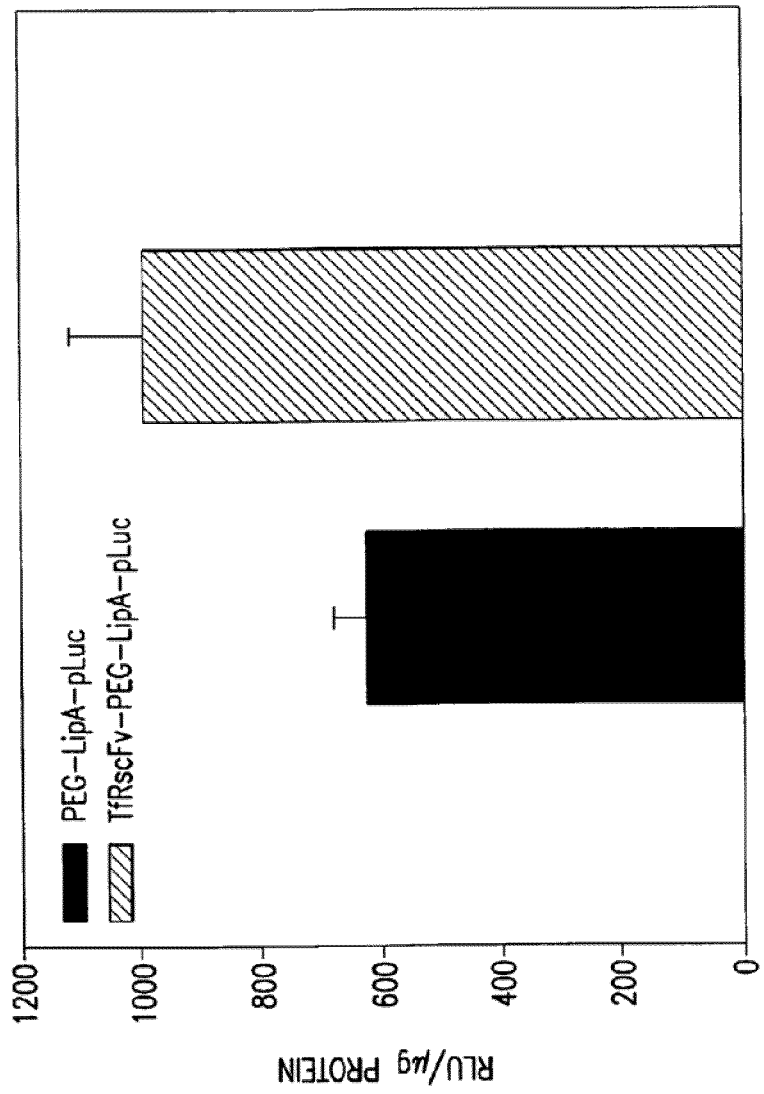

SIMPLIFIED AND IMPROVED METHOD FOR PREPARING AN ANTIBODY OR AN ANTIBODY FRAGMENT TARGETED IMMUNOLIPOSOME FOR SYSTEMIC ADMINISTRATION OF A THERAPEUTIC OR DIAGNOSTIC AGENT

CROSS REFERENCE TO RELATED APPLICATIONS

This application is a divisional application of U.S. application Ser. No. 10/113,927, filed Apr. 2, 2002, now U.S. Pat. No. 7,780,882, which claims benefit of U.S. Provisional Application No. 60/280,134, filed Apr. 2, 2001. U.S. application Ser. No. 10/113,927, is a continuation-in-part application of U.S. application Ser. No. 09/914,046, filed Oct. 1, 2001, now U.S. Pat. No. 7,479,276, which is a §371 Application of PCT/US00/04392, filed Feb. 22, 2000, which claims benefit of U.S. Provisional Application No. 60/121,133, filed Feb. 22, 1999. The disclosures of each of these applications are incorporated by reference herein in their entireties.

BACKGROUND OF THE INVENTION

1. Field of the Invention

This invention provides a method of making antibody- or antibody fragment-targeted immunoliposomes and antibody- or antibody fragment-targeted polymers useful for the systemic delivery of molecules to treat diseases. The liposome and polymer complexes are useful for carrying out targeted gene delivery and efficient gene expression after systemic administration. The specificity of the delivery system is derived from the targeting antibodies or antibody fragments.

2. Background Art

The ideal therapeutic for cancer would be one that selectively targets a cellular pathway responsible for the tumor phenotype and would be nontoxic to normal cells. To date, the ideal therapeutic remains just that—an ideal. While cancer treatments involving gene therapy have substantial promise, there are many issues that need to be addressed before this promise can be realized. Perhaps foremost among the issues associated with macromolecular treatments is the efficient delivery of the therapeutic molecules to the site(s) in the body where they are needed. The ideal delivery vehicle would be one that could be systemically administered and then home to tumor cells wherever they occur in the body. A variety of delivery systems ("vectors") have been tried, including viruses and liposomes. The infectivity that makes viruses attractive as delivery vectors also poses their greatest drawback. Residual viral elements can be immunogenic, cytopathic or recombinogenic. The generation of novel viruses with new targets for infection also raises the theoretical possibility that, once introduced into patients, these viruses could be transformed via genetic alteration into new human pathogens. Consequently, a significant amount of attention has been directed at non-viral vectors for the delivery of molecular therapeutics. The liposome approach offers a number of advantages over viral methodologies for gene delivery. Most significantly, they lack immunogenicity. Moreover, since liposomes are not infectious agents capable of self-replication, they pose no risk of evolving into new classes of infectious human pathogens.

Targeting cancer cells via liposomes can be achieved by modifying the liposomes so that they selectively deliver their payload to tumor cells. Surface molecules can be used to target liposomes to tumor cells, because the molecules that decorate the exterior of tumor cells differ from those on normal cells. For example, if a liposome has the protein transferrin (Tf) or an antibody that recognizes transferrin receptor (TfR) on its surface, it will home to cancer cells that have higher levels of the TfR. Such liposomes designed to home to tumors have been likened to "smart" bombs capable of seeking out their target.

Failure to respond to therapy represents an unmet medical need in the treatment of many types of cancer, including prostate cancer. Often when cancer recurs, the tumors have acquired increased resistance to radiation or chemotherapeutic agents. The incorporation into currently used cancer therapies of a new component which results in radio-/chemo-sensitization would have immense clinical relevance. One way in which such sensitization could be achieved is via gene therapy (i.e., delivery of a gene the expression of which results in increased sensitization). In PCT patent application WO 00/50008 (published 31 Aug. 2000), incorporated herein by reference, we provided proof-of-principle that an anti-transferrin receptor single chain antibody (TfRscFv) can be chemically conjugated to a cationic liposome. Moreover, this TfRscFv directed liposome delivery system can deliver genes and other molecules systemically and specifically to tumors.

Immunoliposomes and Cationic Polymers as Gene Transfer Vehicles

As noted above, some of the problems associated with using viral vectors could be circumvented by non-viral gene transfer vectors. Progress has been made toward developing non-viral, pharmaceutical formulations of genes for in vivo human therapy, particularly cationic liposome-mediated gene transfer systems (31, 32). Cationic liposomes are composed of positively charged lipid bilayers and can be complexed to negatively charged, naked DNA by simple mixing of lipids and DNA such that the resulting complex has a net positive charge. The complex can be bound and taken up by cells in culture with moderately good transfection efficiency (33). Features of cationic liposomes that make them versatile and attractive for DNA delivery include: simplicity of preparation; the ability to complex large amounts of DNA; versatility in use with any type and size of DNA or RNA; the ability to transfect many different types of cells, including non-dividing cells; and lack of immunogenicity or biohazardous activity (reviewed in 34, 35). More importantly from the perspective of human cancer therapy, cationic liposomes have been proven to be safe and efficient for in vivo gene delivery (33, 34, 36). At least 75 clinical trials have been approved using cationic liposomes for gene delivery (37), and liposomes for delivery of small molecule therapeutics (e.g., antifungal agents) are already on the market.

Researchers also have considered the suitability of cationic polymers as transfer vectors for delivery of therapeutic agents in vivo. For example, Polyethyleneimine (PEI) is the organic macromolecule with the highest cationic-charge-density potential, and a versatile vector for gene and oligonucleotide transfer in vitro and in vivo, as first reported by Boussif et al. (66). Since then, there has been a flurry of research aimed at this polycation and its role in gene therapy (73). Cell-binding ligands can be introduced to the polycation to 1) target specific cell types and 2) enhance intracellular uptake after binding the target cell (13). Erbacher et al. (67) conjugated the integrin-binding peptide 9-mer RGD via a disulfide bridge and showed physical properties of interest for systemic gene delivery.

The transfection efficiency of both cationic liposomes and cationic polymers, such as PEI, can be increased dramatically when they bear a ligand recognized by a cell surface receptor. Receptor-mediated endocytosis represents a highly efficient internalization pathway present in eukaryotic cells (38, 39).

The presence of a ligand on a liposome facilitates the entry of DNA into cells through initial binding of ligand by its receptor on the cell surface followed by internalization of the bound complex. Transferrin receptor (TfR) levels are elevated in various types of cancer cells including prostate cancers (40), even those prostate cell lines derived from human lymph node and bone metastases (40-43). Elevated TfR levels also correlate with the aggressive or proliferative ability of tumor cells (44). Therefore, TfR is a potential target for drug delivery in the therapy of malignant cell growth (45, 46). In our laboratory, we have prepared transferrin-complexed cationic liposomes with tumor cell transfection efficiencies in SCCHN of 60%-70%, as compared to only 5-20% by cationic liposomes without ligand (47). Also see published PCT patent application WO 00/50008.

In addition to the use of ligands that are recognized by receptors on tumor cells, specific antibodies also can be attached to the liposome surface (48) enabling them to be directed to specific tumor surface antigens (including but not limited to receptors) (49). These "immunoliposomes," especially the sterically stabilized immunoliposomes, can deliver therapeutic drugs to a specific target cell population (50). Parks et al. (51) found that anti-HER-2 monoclonal antibody (MAb) Fab fragments conjugated to liposomes could bind specifically to a breast cancer cell line, SK-BR-3, that overexpresses HER-2. The immunoliposomes were found to be internalized efficiently by receptor-mediated endocytosis via the coated pit pathway and also possibly by membrane fusion. Moreover, the anchoring of anti-HER-2 Fab fragments enhanced their inhibitory effects. More recently, Park et al. (23) used an anti-HER-2 immunoliposome composed of long circulating liposomes chemically conjugated to anti-HER-2 monoclonal antibody scFv fragments to deliver doxorubicin to breast cancer tumors even though HER-2 was not overexpressed. A number of other studies have been published which have employed antibodies against tumor specific antigens coupled to liposomes, primarily sterically stabilized liposomes, to target tumor cells for delivery of prodrugs and drugs in vitro or in vivo (52-56). These studies demonstrated the utility of immunoliposomes for tumor-targeting drug delivery. The combination of cationic liposome-gene transfer and immunoliposome techniques appears to be a promising system for targeted gene therapy and is the subject of this proposal.

Progress in biotechnology has allowed the derivation of specific recognition domains from MAb (57). The recombination of the variable regions of heavy and light chains and their integration into a single polypeptide provides the possibility of employing single-chain antibody derivatives (designated scFv) for targeting purposes. Thus, a scFv based on the anti-TfR MAb 5E9 (52) contains the complete antibody binding site for the epitope of the TfR recognized by this MAb as a single polypeptide chain of approximate molecular weight 26,000. This TfRscFv is formed by connecting the component VH and VL variable domains from the heavy and light chains, respectively, with an appropriately designed linker peptide. The linker bridges the C-terminus of the first variable region and N-terminus of the second, ordered as either VH-linker-VL or VL-linker-VH. The binding site of an scFv can replicate both the affinity and specificity of its parent antibody combining site.

The TfRscFv has advantages in human use over the Tf molecule itself or even an entire MAb to target liposomes or cationic polymers to prostate cancer cells with elevated levels of the TfR for a number of reasons. First, the size of the scFv (~28 kDa) is much smaller than that of the Tf molecule (~80 kDa) or the parental MAb (~150 kDa). The scFv-liposome-therapeutic agent complex or scFv-polymer-therapeutic agent complex thus may exhibit better penetration into small capillaries characteristic of solid tumors. Second, the smaller scFv also has practical advantages related to its production as a recombinant protein. Large scale production of the TfRscFv will be required for the therapy envisioned in this proposal to be taken into eventual human trials. Third, the scFv is a recombinant molecule (not a blood product like Tf) and, therefore, presents no issues related to potential contamination with blood borne pathogens. Additional advantages of using the TfRscFv relate to the fact that Tf interacts with the TfR with high affinity only after the ligand is loaded with iron. Large-scale production of liposomes containing iron-loaded Tf may present practical challenges. Thus, use of TfRscFv enables the tumor cell TfR to be targeted by a liposomal therapeutic complex that does not contain iron (itself implicated in cancer (58)). Fourth, without the Fc region of the MAb, the problem of non-antigen-specific binding through Fc receptors is eliminated (57).

p53 Tumor Suppressor Gene and the Pathogenesis of Prostate Cancer

The tumor suppressor gene p53 plays a crucial role in diverse cellular pathways including those activated in response to DNA damage, such as DNA repair, regulation of the cell cycle and programmed cell death (apoptosis) (1). Malfunctions of these critical cell pathways are associated with the process of tumorigenesis. Loss of functional p53, which has been implicated in over 60% of human cancers, can occur either through mutations in the p53 gene itself (the most common occurrence), or through other mechanisms such as amplification of the MDM-2 gene (found in certain sarcomas, and other cancers), or association of p53 with the E6 protein of human papilloma virus (which likely plays a role in cervical carcinoma) (2).

The loss of p53 function is of relevance to a broad array of cancer types, with non-functional p53 associated with, for example, 15-50% of breast cancer, 25-70% of metastatic prostate cancer, 25-75% of lung cancer, and 33-100% of head and neck cancers (3). The presence of mutant p53 also has been associated with an unfavorable prognosis for many human cancers including lung, colon, and breast (3), and mutant p53 is rarely found in some of the most curable forms of cancer e.g., Wilm's tumor, retinoblastoma, testicular cancer, neuroblastoma and acute lymphoblastic leukemia (4). In addition, p53 protein transcriptionally regulates genes involved in angiogenesis, a process required for solid tumor growth (5). Volpert et al. have proposed that development of the angiogenic phenotype for these tumors requires the loss of both p53 alleles (6).

Since it appears that most anti-cancer agents work by inducing apoptosis (20), inhibition of or changes in this pathway may lead to failure of therapeutic regimens. A direct link has been suggested between mutations in p53 and resistance to cytotoxic cancer treatments (both chemo- and radiotherapy (21)). It has also been suggested that the loss of p53 function may contribute to the cross-resistance to anti-cancer agents observed in some tumor cells (22).

Restoration of p53 function could, therefore result in sensitization of primary prostate tumors and even metastases to radio-/chemo-therapy. The introduction of wtp53 has been reported to suppress, both in vitro and in mouse xenograft models, the growth of various types of malignancies, e.g., prostate (23, 24), head and neck (25, 26), colon (27), cervical (28) and lung (15, 29) tumor cells. However, p53 alone, while being able to partially inhibit tumor growth, has not been shown to be able to eliminate established tumors. Significantly, however, we have demonstrated that the combination of systemically delivered liposome-p53 and radiation led to complete long-term tumor regression of established head and neck xenograft tumors (25, 30).

In summary, the implication of the p53 gene in a significant fraction of human cancers makes it one of the premiere candidates for cancer gene therapy. Based on a growing body of evidence related to p53 functions, effective restoration of these functions in tumor cells might be expected to re-establish normal cell growth control, restore appropriate responses to DNA-damaging agents (e.g., chemotherapy and radiotherapy), and to impede angiogenesis.

The sensitization of tumors to chemotherapy and radiation could lower the effective dose of both types of anticancer modalities, correspondingly lessening the severe side effects often associated with these treatments. Until now the vast majority of p53 gene therapy protocols have employed wtp53 gene replacement alone. Based upon the current literature and our data (30, 59), it appears that wtp53 replacement alone, while able to inhibit tumor growth to some extent, is insufficient to eliminate tumors long term. Therefore, it appears that a combinatorial approach involving both standard therapy and targeted gene therapy has substantial promise as a novel and more effective clinical modality for cancer treatment. Moreover, the demonstrated tumor cell selectivity of our systemically delivered ligand-liposome wtp53 complex indicates the potential of this method to sensitize even the distant micrometastases that are the ultimate cause of so many prostate cancer deaths.

BRIEF SUMMARY OF THE INVENTION

In accordance with this invention a variety of immunoliposomes and polymer complexes have been constructed that are capable of tumor-targeted, systemic delivery of a variety of types of therapeutic molecules for use in treating human diseases. The antibody- or antibody fragment-targeted immunoliposomes or polymer complexes are made via a simple and efficient non-chemical conjugation method. These complexes are equally as effective as, or more effective than, similar complexes prepared by chemical conjugation of the antibody or antibody fragment to the liposome or polymer complex. If an antibody fragment is used, the resultant complex is capable of producing a much higher level of transfection efficiency than the same liposome-therapeutic agent or polymer-therapeutic agent complex bearing the complete antibody molecule.

In accordance with the present invention, the single chain protein is not chemically conjugated to the liposome or polymer. Rather, the antibody- or scFv-liposome-therapeutic or diagnostic agent complex or the antibody- or scFv-polymer-therapeutic or diagnostic agent complex is formed by simple mixing of the components in a defined ratio and order. In one embodiment, the antibody or single chain protein first is mixed with the cationic liposome or the polymer at a protein:lipid ratio in the range of about 1:20 to about 1:40 (w:w) or protein:polymer ratio in the range of about 0.1:1 to 10:1 (molar ratio). The antibody- or antibody fragment-liposome or antibody- or antibody fragment-polymer then is mixed with a desired therapeutic or diagnostic agent, such as nucleic acid (preferably DNA), at a ratio in the range of about 1:10 to 1:20 (µg therapeutic or diagnostic agent:nmole total lipid) or about 1:1 to 1:40 (ug therapeutic or diagnostic agent:nmole polymer) and incubated for 10-15 minutes at room temperature.

The resultant therapeutic or diagnostic agent-antibody-liposome or therapeutic agent-antibody-polymer complex can be administered to a mammal, preferably a human, to deliver the agent to target cells in the mammal's body. Desirably the complexes are targeted to a site of interest can be a cell which is a cancer cell or a non-cancer cell. The targeting agent is an antibody or antibody fragment, which in one preferred embodiment binds to a transferrin receptor, and the target cell is a cell which expresses or contains the target site of interest. If the antibody or antibody fragment binds to a transferrin receptor, the target cell is a cell which expresses a transferrin receptor. The therapeutic agent can be a nucleic acid, preferably a DNA molecule and more preferably a DNA molecule which encodes a wild type p53 molecule, Rb molecule or Apoptin molecule or an antisense HER-2. The complexes, preferably in a therapeutic composition, can be administered systemically, preferably intravenously.

BRIEF DESCRIPTION OF THE DRAWINGS/FIGURES

FIGS. 6A and 6B show the results of an XTT cytotoxicity assay showing the chemosensitivity to gemcitabine HCl (GEMZAR®) induced in pancreatic cancer cell lines (Colo 357 and Panc I) treated with TfRscFv-liposome-p53 prepared by simple mixing.

FIG. 12 shows the results of an in vitro transfection assay of sterically stabilized TfRscFv-PEG-liposome A-pLuc in MDA-MB-435 cells (Luciferase assay).

DETAILED DESCRIPTION OF THE INVENTION

Figure 1:
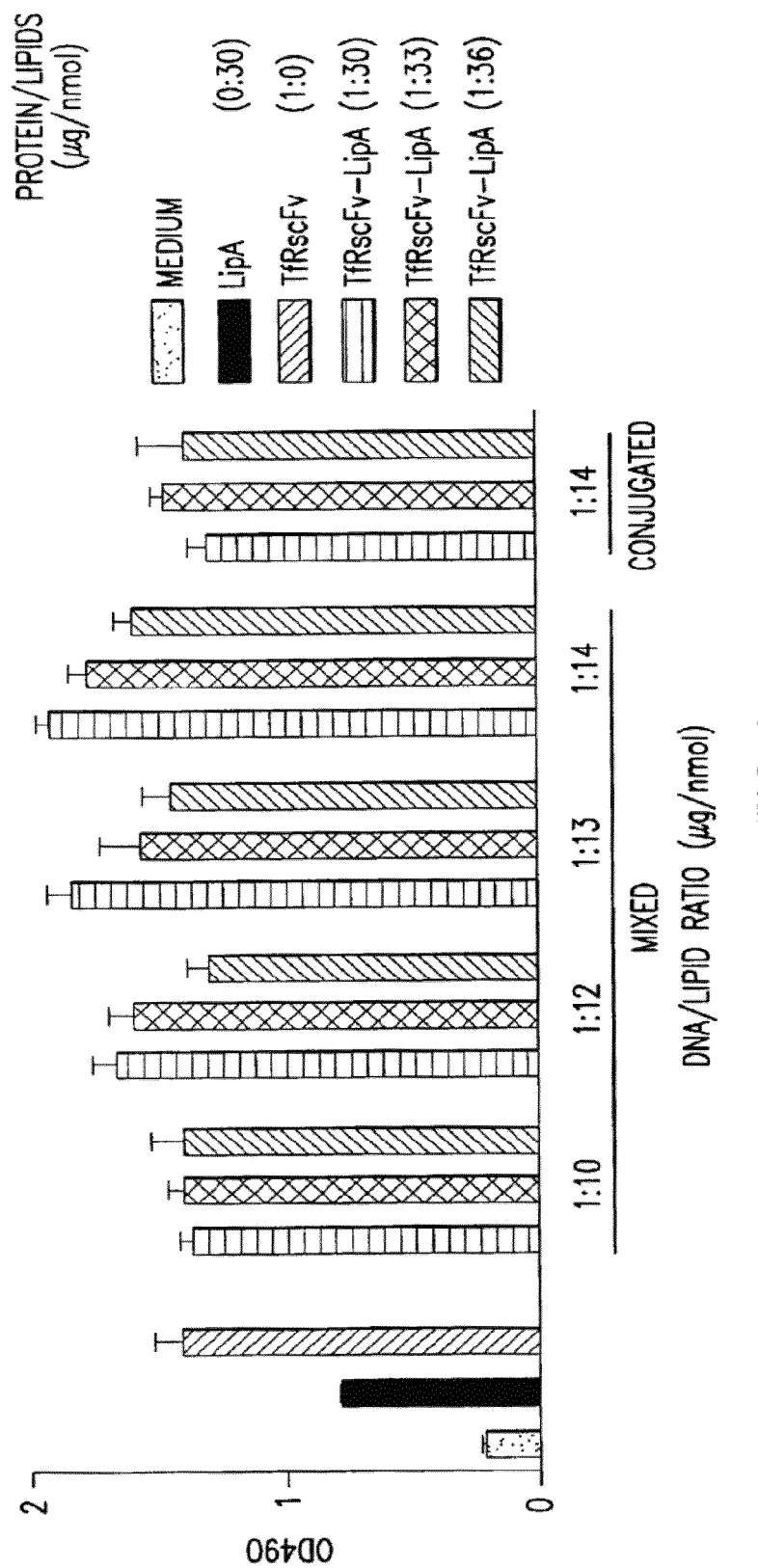
FIG. 1 shows the results of an ELISA assay showing binding of TfRscFv-liposome-DNA complex, made by simple mixing, to DU145 cells at various ratios of protein/lipid and DNA/lipid.

Antibody- or antibody fragment-targeted cationic liposome or cationic polymer complexes in accordance with this invention are made by a simple and efficient non chemical conjugation method in which the components of the desired complex are mixed together in a defined ratio and in a defined order. The resultant complexes are as effective as, or more effective than, similar complexes in which the antibody or antibody fragment is chemically conjugated to the liposome or polymer.

Either a whole antibody or an antibody fragment can be used to make the complexes of this invention. In a preferred embodiment, an antibody fragment is used. Preferably, the antibody fragment is a single chain Fv fragment of an antibody. One preferred antibody is an anti-TfR monoclonal antibody and a preferred antibody fragment is an scFv based on an anti-TfR monoclonal antibody. A suitable anti-TfR monoclonal antibody is 5E9. Another preferred antibody is an anti-HER-2 monoclonal antibody, and another preferred antibody fragment is an scFv based on an anti-HER-2 monoclonal antibody. An scFv based on this antibody contains the complete antibody binding site for the epitope of the TfR recognized by this MAb as a single polypeptide chain of approximate molecular weight 26,000. An scFv is formed by connecting the component VH and VL variable domains from the heavy and light chains, respectively, with an appropriately designed linker peptide, which bridges the C-terminus of the first variable region and N-terminus of the second, ordered as either VH-linker-VL or VL-linker-VH.

In a preferred embodiment, a cysteine moiety is added to the C-terminus of the scFv. Although not wishing to be bound by theory, it is believed that the cysteine, which provides a free sulfhydryl group, may enhance the formation of the complex between the antibody and the liposome. With or without the cysteine, the protein can be expressed in E. coli inclusion bodies and then refolded to produce the antibody fragment in active form, as described in detail in the Examples below.

Unless it is desired to use a sterically stabilized immunoliposome in the formation of the complex, a first step in making the complex comprises mixing a cationic liposome or combination of liposomes or small polymer with the antibody or antibody fragment of choice. A wide variety of cationic liposomes are useful in the preparation of the complexes of this invention. Published PCT application WO99/25320 describes the preparation of several cationic liposomes. Examples of desirable liposomes include those that comprise a mixture of dioleoyltrimethylammonium phosphate (DOTAP) and dioleoylphosphatidylethanolamine (DOPE) and/or cholesterol (chol), a mixture of dimethyldioctadecylammonium bromide (DDAB) and DOPE and/or chol. The ratio of the lipids can be varied to optimize the efficiency of uptake of the therapeutic molecule for the specific target cell type. The liposome can comprise a mixture of one or more cationic lipids and one or more neutral or helper lipids. A desirable ratio of cationic lipid(s) to neutral or helper lipid(s) is about 1:(0.5-3), preferably 1:(1-2) (molar ratio).

Suitable polymers are DNA binding cationic polymers that are capable of mediating DNA compaction and can also mediate endosome release. A preferred polymer is polyethyleneimine. Other useful polymers include polysine, protamine and polyamidoamine dendrimers.

The antibody or antibody fragment is one which will bind to the surface of the target cell, and preferably to a receptor that is differentially expressed on the target cell. The antibody or antibody fragment is mixed with the cationic liposome or polymer at room temperature and at a protein:lipid ratio in the range of about 1:20 to about 1:40 (w:w) or a protein polymer ratio in the range of about 0.1:1 to 10:1 (molar ratio).

The antibody or antibody fragment and the liposome or polymer are allowed to incubate at room temperature for a short period of time, typically for about 10-15 minutes, then the mixture is mixed with a therapeutic or diagnostic agent of choice. Examples of therapeutic molecules or agents which can be complexed to the antibody and liposome include genes, high molecular weight DNA (genomic DNA), plasmid DNA, antisense oligonucleotides, peptides, ribozymes, nucleic acids, viral particles, immunomodulating agents, proteins and chemical agents. Preferred therapeutic molecules include genes encoding p53, Rb94 or Apoptin. RB94 is a variant of the retinoblastoma tumor suppressor gene. Apoptin is a gene that induces apoptosis in tumor cells only. In another preferred embodiment, the agent is an antisense oligonucleotide, such as HER-2. A preferred HER-2 antisense oligonucleotide has the sequence 5'-TCC ATG GTG CTC ACT-3' (Seq. ID No: 1). A third type of preferred agent is a diagnostic imaging agent, such as an MRI imaging agent, such as a Gd-DTPA agent. If the agent is DNA, such as the coding region of p53, it can be positioned under the control of a strong constitutive promoter, such as an RSV or a CMV promoter.

The antibody or antibody fragment and liposome combination is mixed with the therapeutic or diagnostic agent at a ratio in the range of about 1:10 to 1:20 (μg of agent:nmole of total lipid) or 1:10 to 1:40 (ug of agent:nmole of total polymer) and incubated at room temperature for a short period of time, typically about 10 to 15 minutes. The size of the liposome complex is typically within the range of about 50-400 nm as measured by dynamic light scattering using a dynamic light scattering instrument (Malvern ZETASIZER® 3000).

In one embodiment of this invention, the liposome used to form the complex is a sterically stabilized liposome. Sterically stabilized liposomes are liposomes into which a hydrophilic polymer, such as PEG, poly(2-ethylacrylic acid), or poly(n-isopropylacrylamide (PNIPAM) have been integrated. Such modified liposomes can be particularly useful when complexed with therapeutic or diagnostic agents, as they typically are not cleared from the blood stream by the reticuloendothelial system as quickly as are comparable liposomes that have not been so modified. To make a sterically stabilized liposome complex of the present invention, the order of mixing the antibody or antibody fragment, the liposome and the therapeutic or diagnostic agent is reversed from the order set forth above. In a first step, a cationic liposome as described above is first mixed with a therapeutic or diagnostic agent as described above at a ratio in the range of about 1:10 to 1:20 (μg of agent:nmole of lipid). To this lipoplex is added a solution of a PEG polymer in a physiologically acceptable buffer and the resultant solution is incubated at room temperature for a time sufficient to allow the polymer to integrate into the liposome complex. The antibody or antibody fragment then is mixed with the stabilized liposome complex at room temperature and at a protein:lipid ratio in the range of about 1:5 to about 1:30 (w:w).

The liposomal or polymer complexes prepared in accordance with the present invention can be formulated as a pharmacologically acceptable formulation for in vivo administration. The complexes can be combined with a pharmacologically compatible vehicle or carrier. The compositions can be formulated, for example, for intravenous administration to a human patient to be benefited by administration of the therapeutic or diagnostic molecule of the complex. The complexes are sized appropriately so that they are distributed throughout the body following i.v. administration. Alternatively, the complexes can be delivered via other routes of administration, such as intratumoral, intralesional, aerosal, percutaneous, endoscopic, topical or subcutaneous administration.

In one embodiment, compositions comprising the antibody- or antibody fragment-targeted liposome (or polymer) and therapeutic agent complexes are administered to effect human gene therapy. The therapeutic agent component of the complex comprises a therapeutic gene under the control of an appropriate regulatory sequence. Gene therapy for various forms of human cancers can be accomplished by the systemic delivery of antibody or antibody fragment-targeted liposome or polymer complexes which contain a nucleic acid encoding wt p53. The complexes can specifically target and sensitize tumor cells, both primary and metastatic tumors, to radiation and/or chemotherapy both in vitro and in vivo.

The complexes can be optimized for target cell type through the choice and ratio of lipids, the ratio of antibody or antibody fragment to liposome, the ratio of antibody or antibody fragment and liposome to the therapeutic or diagnostic agent, and the choice of antibody or antibody fragment and therapeutic or diagnostic agent.

In one embodiment, the target cells are cancer cells. Although any tissue having malignant cell growth can be a target, head and neck, breast, prostate, pancreatic, glioblastoma, cervical, lung, liposarcoma, rhabdomyosarcoma, choriocarcinoma, melanoma, retinoblastoma, ovarian, gastric and colorectal cancers are preferred targets.

The complexes made by the method of this invention also can be used to target non-tumor cells for delivery of a therapeutic molecule. While any normal cell can be a target, preferred cells are dendritic cells, endothelial cells of the blood vessels, lung cells, breast cells, bone marrow cells and liver cells. Undesirable, but benign, cells can be targeted, such as benign prostatic hyperplasia cells, over-active thyroid cells, lipoma cells, and cells relating to autoimmune diseases, such as B cells that produce antibodies involved in arthritis, lupus, myasthenia gravis, squamous metaplasia, dysplasia and the like.

The complexes can be administered in combination with another therapeutic agent, such as either a radiation or chemotherapeutic agent. The therapeutic agent, or a combination of therapeutic agents, can be administered before or subsequent to the administration of the complex, for example within about 12 hours to about 7 days. Chemotherapeutic agents include, for example, doxorubicin, 5-fluorouracil (5FU), cisplatin (CDDP), docetaxel, gemcitabine, pacletaxel, vinblastine, etoposide (VP-16), camptothecin, actinomycin-D, mitoxantrone and mitomycin C. Radiation therapies include gamma radiation, X-rays, UV irradiation, microwaves, electronic emissions and the like.

Diagnostic agents also can be delivered to targeted cells via the liposome or polymer complexes. Agents which can be detected in vivo following administration can be used. Exemplary diagnostic agents include electron dense materials, magnetic resonance imaging agents and radiopharmaceuticals. Radionuclides useful for imaging include radioisotopes of copper, gallium, indium, rhenium, and technetium, including isotopes $^{64}$Cu, $^{67}$Cu, $^{111}$In, $^{99m}$Tc, $^{67}$Ga or $^{68}$Ga. Imaging agents disclosed by Low et al. in U.S. Pat. No. 5,688,488, incorporated herein by reference, are useful in the present invention.

The complexes made in accordance with the method of this invention can be provided in the form of kits for use in the systemic delivery of a therapeutic molecule by the complex. Suitable kits can comprise, in separate, suitable containers, the liposome, the antibody or antibody fragment, and the therapeutic or diagnostic agent. The components can be mixed under sterile conditions in the appropriate order and administered to a patient within a reasonable period of time, generally from about 30 minutes to about 24 hours, after preparation. The kit components preferably are provided as solutions or as dried powders. Components provided in solution form preferably are formulated in sterile water-for-injection, along with appropriate buffers, osmolarity control agents, etc.

The invention is illustrated by the following examples, which are not intended to be limiting.

EXAMPLES

Example 1

Construction and Purification of TfRscFv with a 3'-Cysteine

Plasmid expression vector pDFH2T-vecOK was obtained from Dr. David Fitzgerald, NCI. This vector encodes the single chain fragment for the 5E9 antibody, which recognizes the human transferrin receptor (CD71). The VH-linker-Vκ TfRscFv was obtained by PCR amplification of the desired fragment. A cysteine moiety was added at the 3' end of the TfRscFv protein. Two forms of this vector were constructed. The first contains a pelB leader signal sequence, for transport to the periplasmic space, and a His Tag. The presence of the His Tag aids in detection of the protein, thus simplifying development of the purification protocol. Although this form was used for the initial testing, FDA guidelines recommend that no extraneous sequences be present for use in clinical trials. Therefore, a second form minus both of these sequences also was made.

Using PCR amplification the nucleotide sequence for the cysteine residue and a NotI restriction site were introduced at the 3' end. Similarly, a 5' NcoI site also was incorporated. The PCR product was cloned into NcoI and NotI sites of the commercial vector pET26b(+) (Novagen) thus producing a protein product containing both the pelB leader signal sequence and the His Tag. Growth in bacterial culture containing IPTG yielded an approximate 100 fold increase in single chain protein expression which was maximum at approximately 10 hours of IPTG induction. This protein was found primarily in the insoluble fraction (inclusion bodies).

The above construct also was modified to eliminate both the His Tag and pelB sequences in the final protein product. To accomplish this, the pET26b(+) vector was cut at the Nde I enzyme site 5' of the pelB sequence. PCR amplification inserted an Nde I site at the 5' end of the VH-linker-Vκ scFv for the TfR sequence. In addition to the nucleotide sequence for the cysteine residue and the NotI restriction site at the 3' end, a DNA stop codon was introduced adjacent to the cysteine sequence and before the NotI site. The PCR product was cloned into the NdeI and NotI sites of commercial expression vector pET26b(+) (Novogen). Thus, the protein product of this construct will not contain either the pelB sequence or the His-tag.

The majority of the cys-TfRscFv protein (approximately 90%) was found not to be soluble but to be contained within inclusion bodies. Therefore, the protein from the constructs described above was isolated from the inclusion bodies by sonication, treatment with 6 M guanidine-HCl, 200 mM NaCl (6 M GuHCl buffer) and purified via Sephacryl S-200 gel filtration column chromatography. Refolding of the cys-TfRscFv protein was accomplished by dialysis at 4° C. against decreasing concentrations of guanidine-HCl. After purification, SDS-PAGE showed a single band of the solubilized, refolded cys-TfRscFv protein with the correct molecular weight of approximately 28-30 kDa (as described in WO 00/50008). The cys-TfRscFv protein is stored at −80° C.

Example 2

Preparation of cys-TfRscFv-Liposome by Simple Mixing

Published PCT application WO 99/25320, incorporated herein by reference, describes the preparation of several cationic liposomes. The cationic liposomes prepared are clear solutions, their compositions and ratios are as follows:

| LipA | DOTAP/DOPE | 1:1 molar ratio |
| LipB | DDAB/DOPE | 1:1 molar ratio |
| LipC | DDAB/DOPE | 1:2 molar ratio |
| LipD | DOTAP/Chol | 1:1 molar ratio |
| LipE | DDAB/Chol | 1:1 molar ratio |
| LipG | DOTAP/DOPE/Chol | 2:1:1 molar ratio |
| LipH | DDAB/DOPE/Chol | 2:1:1 molar ratio |

(DOTAP = dioleoyltrimethylaminnonium phosphate, DDAB = dimethyldioctadecylammonium bromide; DOPE = dioleoylphosphatidylethanolamine; chol = cholesterol)

It is well known by those knowledgeable in the field that conjugated TfRscFv-immunoliposome retains its immunologic activity. We have established that the cys-TfRscFv can be chemically conjugated to lipoplex (PCT application WO 00/50008) and can efficiently transfect human prostate tumor cells in vitro and in vivo. It is common practice for single chain antibody fragments to be attached to liposomes using various chemical conjugation methods. We performed studies to determine if a simple mixing of the cys-TfRscFv and the cationic liposome, instead of chemical conjugation, would result in formation of an immunologically active complex that could still efficiently bind to and transfect tumor cells. A series of cys-TfRscFv-immunoliposome complexes was prepared by mixing the cys-TfRscFv with liposome A at defined ratios of single chain protein to liposome ranging from 1/25 to 1/36 (w/w). Based upon the ELISA data with the conjugated cys-TfRscFv complex the ratio of DNA to n moles total lipid in the mixed complex also was varied from 1/8 to 1/18. The preparation of the complexes was in accordance with the following general procedure: The appropriate amount of 2 mM liposome (A-H described above) is mixed with any water required to give a desired volume and inverted to mix. To the liposome-water the appropriate amount of cys-TfRscFv is added to give the desired ratio and mixed by gentle inversion 5-10 seconds. This mixture is kept at room temperature for 10 minutes (again inverted gently for 5-10 seconds after approximately 5 minutes). At the same time, the appropriate amount of DNA is mixed by inversion for 5-10 seconds with any water required to give a desired volume. Typically, for use in an in vitro assay, it is desirable that the concentration of DNA is in the range of about 0.01 µg to about 2 µg per well; for in vivo use, it is desirable to provide about 5 µg to about 50 µg of DNA per injection. The DNA solution is quickly added to the cys-TfRscFv-liposome solution and the mixture is inverted for 5-10 seconds. The final mixture is kept at room temperature for 10 minutes, gently inverting again for 5-10 seconds after approximately 5 minutes. For use in vivo 50% dextrose is added to a final concentration of 5% (V:V) and mixed by gentle inversion for 5-10 seconds. A specific example at a preferred ratio of 1:30 (cys-TfRscFv:liposome, w:w) and 1:14 (µg DNA:n mole total Lipid) is as follows: For 40 µg of DNA in a final volume of 800 µl mix 183 µl water with 280 µl of 2 mM liposome solution. Add 34 µl of cys-TfRscFv (with a concentration of 0.4 µg/ml). Mix 183 µl water with 40 µl of 1 µg/1 µl DNA. Add 80 µl of 50% Dextrose as the last step.

The size of the final complex prepared by the method of this invention is between 100 and 400 nm with a zeta potential of between 25 and 35 as determined by dynamic light scattering using a dynamic light scattering instrument (Malvern ZETASIZER® 3000). This size is small enough to efficiently pass through the tumor capillary bed and reach the tumor cells.

Figure 2:
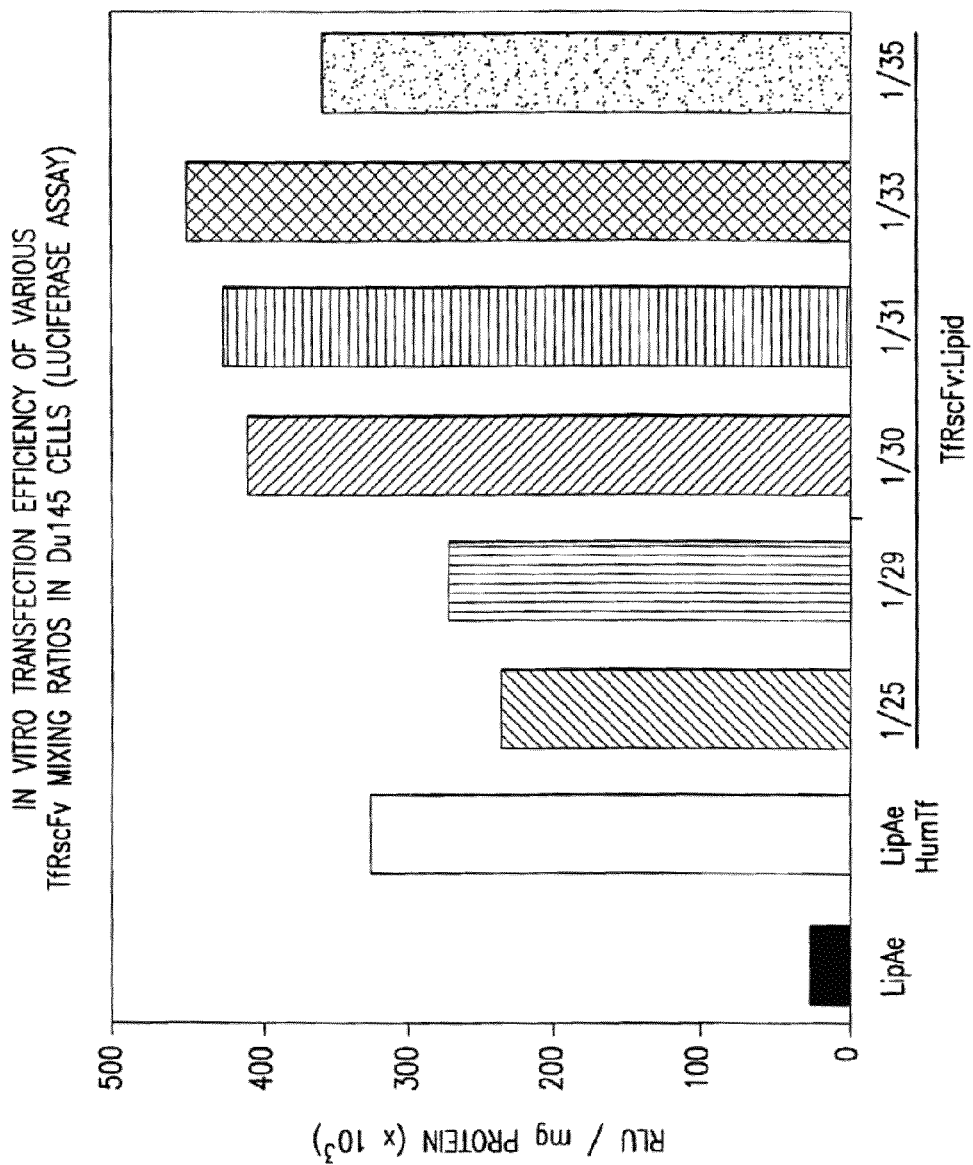
FIG. 2 shows the results of an in vitro transfection assay using different mixing ratios of TfRscFv:lipid in DU145 cells (Luciferase assay).
Figure 3:
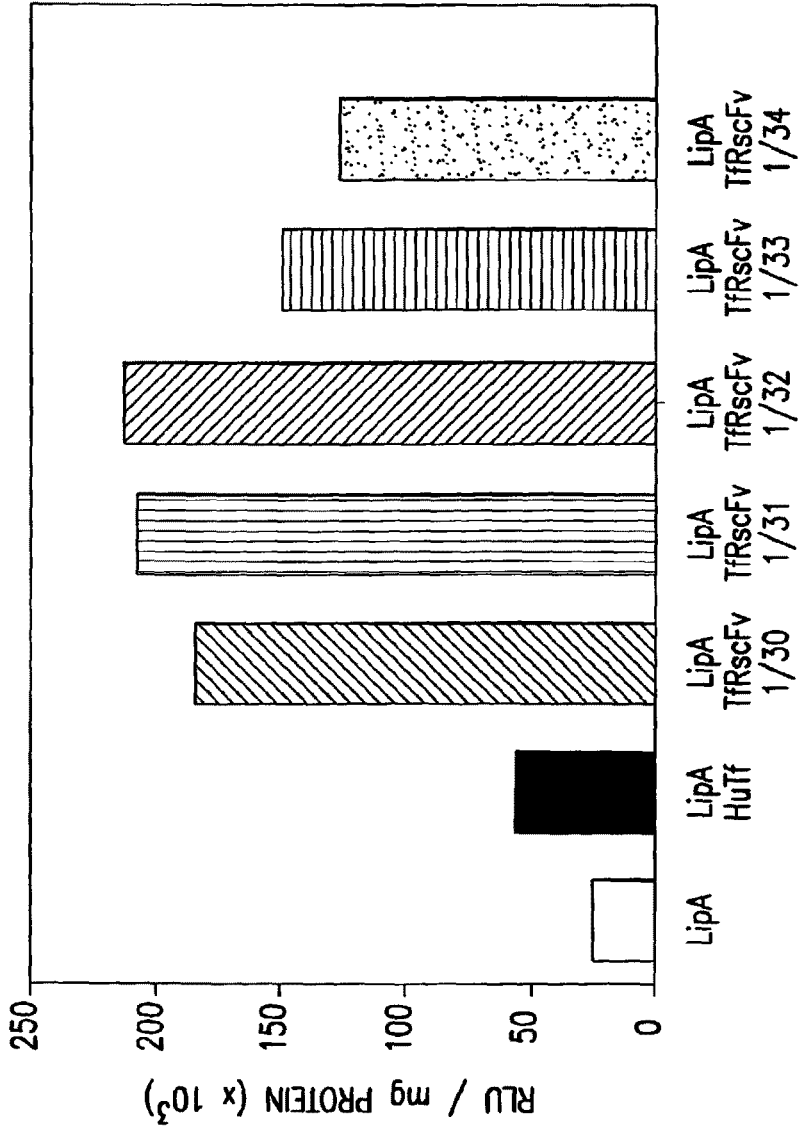
FIG. 3 shows the results of an in vitro transfection assay using different mixing ratios of TfRscFv:lipid in rat C6 cells (Luciferase assay).

An ELISA assay to assess the binding ability of the mixed complex to human prostate cancer DU145 cells was performed. For comparison, the complexes made with the conjugated immunoliposome were also included in the assay. The results shown in FIG. 1 clearly demonstrate that the immunoliposome complex prepared by simple mixing of the cys-TfRscFv protein with the cationic liposome binds to DU145 cells at least as well as those prepared through conjugation. Similar to the conjugated complex, a ratio of 1/30 protein to lipid and 1/14 DNA to lipid was found to have the highest binding ability. As was also previously observed with the conjugated complexes, the binding decreased in a DNA dose dependent manner. These findings indicate that simple mixing of components can form a complex that retains its immunologic activity. Identical optimal ratios were found in human prostate DU145 cells, and RAT C6 cells using the Luciferase assay (FIGS. 2 and 3) and in human pancreatic cancer cell line Panc I (Table I, II) using enhanced green fluorescence protein (EGFP) to assess the transfection efficiency.

TABLE I

Transfection Efficiency of cys-TfRscFv-Liposome A in Panc I Cells Prepared by Simple Mixing Assessed Using the EGFP Reporter Gene I

| Ratio DNA:Total Lipids (µg: n moles) | % Fluorescent Cells |
| --- | --- |
| 1:8 | 20 |
| 1:10 | 22 |
| 1:12 | 35 |
| 1:14 | 50 |
| 1:16 | 24 |
| 1:18 | 20 |

The ratio of cys-TfRscFv:Liposome was 1:3 (w:w)

TABLE II

Transfection Efficiency of cys-TfRscFv-Liposome A in Panc I Cells Prepared by Simple Mixing Assessed Using the EGFP Reporter Gene II

| Ratio cys-TfRscFv:Lipids (w:w) | % Fluorescent Cells |
| --- | --- |
| 1:26 | 14 |
| 1:28 | 14 |
| 1:30 | 30 |
| 1:32 | 28 |

TABLE II-continued

Transfection Efficiency of cys-TfRscFv-Liposome
A in Panc I Cells Prepared by Simple Mixing
Assessed Using the EGFP Reporter Gene II

| Ratio cys-TfRscFv:Lipids (w:w) | % Fluorescent Cells |
|---|---|
| 1:34 | 15 |
| 1:36 | 18 |

Figure 4:
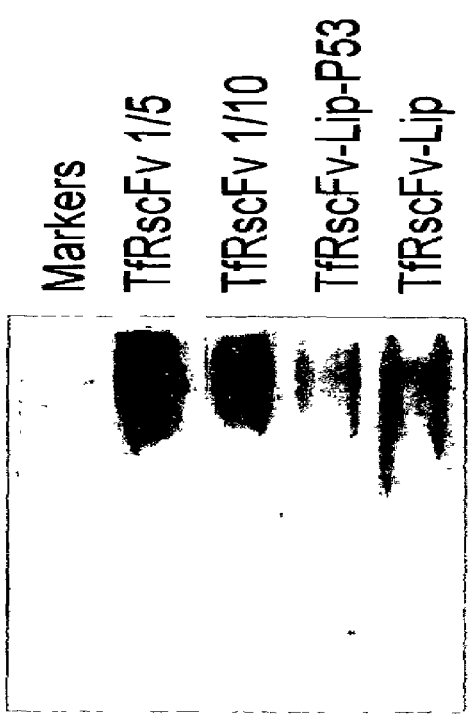
FIG. 4 shows a non-denaturing polyacrylamide gel demonstrating that >95% of the TfRscFv is bound to the liposome or liposome-p53 after simple mixing.

To establish the efficiency of the binding of the cys-TfRscFv to the liposome complex by simple mixing, a non-denaturing polyacylamide gel was used. Mixed cys-TfRscFv-liposome A-p53 complex and cys-TfRscFv-Liposome A without p53 DNA were loaded on the gel along with free cys-TfRscFv in amounts equal to 1/5 or 1/10 the amount of cys-TfRscFv used to prepare the complexes. The complexes were prepared using the ratio of cys-TfRscFv:liposome of 1:30 (w:w) and DNA:total lipid of 1:14 (μg:n mol total lipid). The free cys-TfRscFv complexes serve as quantitation standards, since under non-denaturing conditions the complex can not enter the gel, only free, unbound cys-TfRscFv can migrate into it. After transferring to membrane, the gel was probed with an anti-cys-TfRscFv antibody using the ECL Western Blot detection kit (Amersham). Comparison of the low signal level for the two complexes (with and without p53 DNA) shown in FIG. 4 with the signals from the free cys-TfEscFv standards indicates that greater than 95% of the cys-TfRscFv is incorporated into the complex by simple mixing of the components.

Example 3

In Vitro Chemosensitization of Human Cancer Cell Lines by cys-TfRscFv-Immunoliposome Delivered wtp53

Figure 5A:
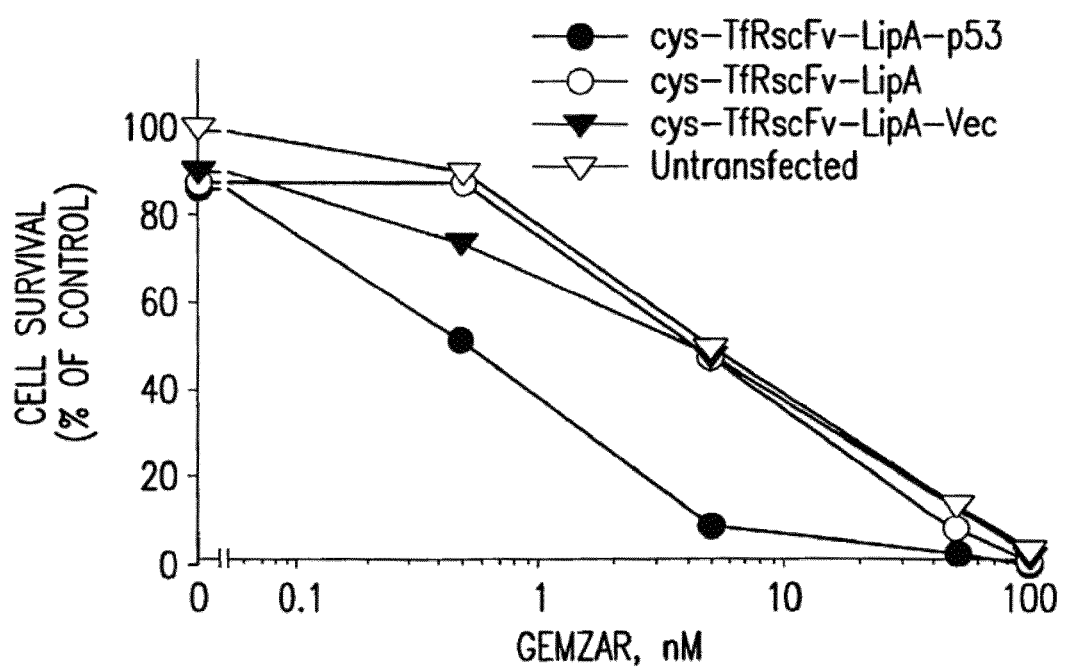
FIG. 5A shows the results of an XTT cytotoxicity assay showing the chemosensitivity to gemcitabine HCl (GEMZAR®) induced in DU145 cells treated with TfRscFv-liposome-p53 prepared by simple mixing.

Experiments were performed to determine how effective the cys-TfRscFv-Liposome-p53 complex prepared by simple mixing would be in sensitizing prostate tumor cells to the drugs GEMZAR® (gemcitabine HCl; manufactured by Eli Lilly and Co.) and NOVANTRONE® (mitoxantrone, Immunex Corp.) both of which currently are used for the treatment of prostate cancer. The prostate tumor cell line DU145, which harbors mutant p53, was employed in these studies. The XTT cytotoxicity assay (66) was used to establish the level of chemosensitivity induced by the cys-TfRscFv-Liposome-p53 complex of this invention. $5 \times 10^3$ DU145 cells were plated/well of a 96 well plate. After 24 hours, the cells were transfected with the mixed cys-TfRscFv-Liposome-p53 complex. The cys-TfRscFv-Liposome-p53 complex was prepared by mixing at a ratio of 1:30 (w:w) (cys-TfRscFv:Liposome A) and 1:14 (μg p53 DNA:n moles total lipid). One day after transfection, anti-neoplastic agents were added at increasing concentrations (in triplicate). The XTT assay was performed approximately 3 days later and $IC_{50}$ values, the drug concentration yielding 50% growth inhibition, calculated. As shown in FIG. 5A, treatment with the cys-TfRscFv-Liposome-p53 complex increased the sensitivity of the cells to GEMZAR® (gemcitabine HCl) by 8-fold. For FIG. 5A, the $IC_{50}$ Values (nM) are as follows: cys-TfRscFv-LipA-p53: 0.5; cys-TfRscFv-LipA: 4.0; cys-TfRscFv-LipA-Vec: 4.0; Untransfected: 5.0. The fold sensitization for Vec vs p53=8 and for UT vs p53=10.

Figure 5B:
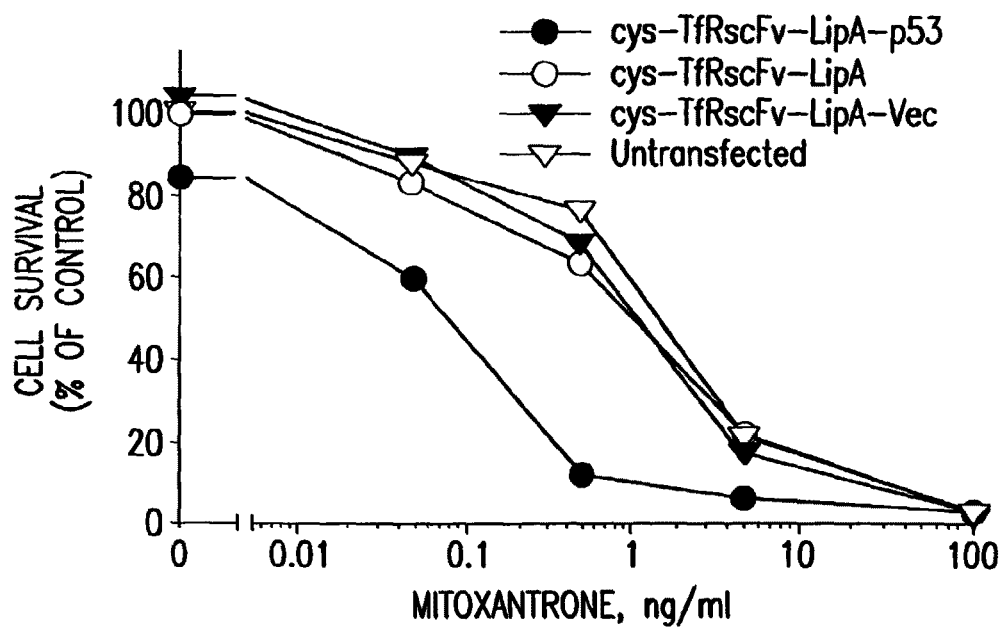
FIG. 5B shows the results of an XTT cytotoxicity assay showing the chemosensitivity to mitoxantrone induced in DU145 cells treated with TfRscFv-liposome-p53 prepared by simple mixing.
Figure 6A:
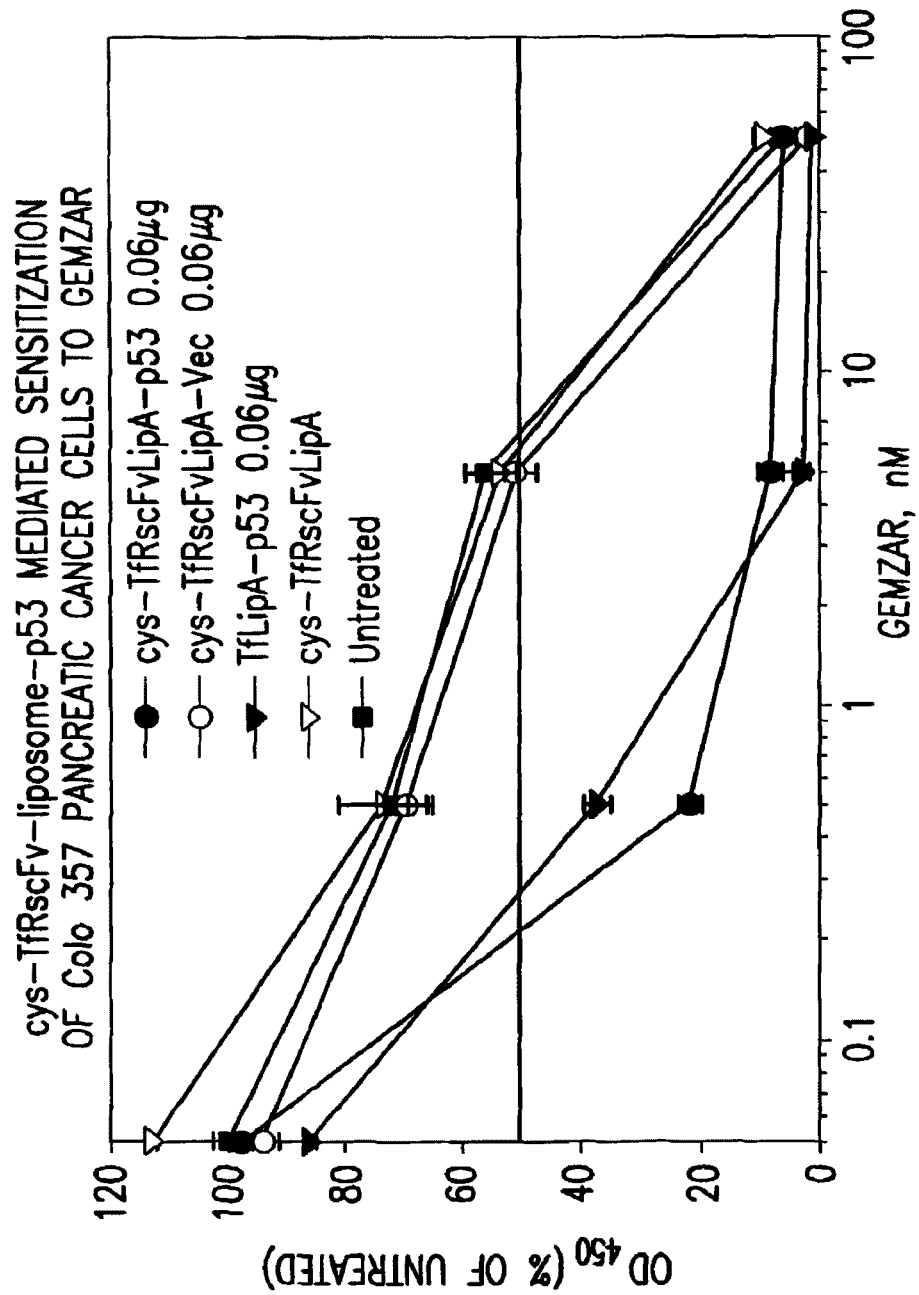

Similarly, DU145 cells were sensitized to the drug mitoxantrone by 17.5-fold (FIG. 5B). For FIG. 5B, the $IC_{50}$ values (ng/ml) were as follows: cys-TfRscFv-LipA-p53: 0.08; cys-TfRscV-LipA: 1.20; cys-TfRscFv-LipA-Vec: 1.40 and Untransfected: 1.80. The fold sensitization for Vec vs p53=17.5 and for UT vs p53=22.5. Similar studies were performed using human pancreatic cancer cell line Panc I. $4 \times 10^3$ Panc I cells per well were plated, and the XTT assay performed as above. A preferred ratio of 1:30 (cys-TfRscFv:liposome A w:w) and 1:14 (μg p53 DNA:n moles total lipid) also was used here. As with DU145 there was significant sensitization of the tumor cells to chemotherapeutic agents (FIGS. 6A and B). At a p53 DNA concentration of 0.06 μg/well there was a 23.8 fold increase in sensitization to GEMZAR® (gemcitabine HCl) using the mixed cys-TfRscFv-liposome DNA complex (FIG. 6A). For FIG. 6A, the $IC_{50}$ values were as follows: cys-TfRscFvLipA-p53: 0.21 nM; cys-TfRscFvLipA-Vec: 5.00 nM and TfLipA-p53: 0.30 nM. The $IC_{50}$ of cys-TfRscFvLipA-Vec/$IC_{50}$ of cys-TfRscFrLipA-p53=23.8. No sensitization was observed when empty vector in place of p53 was used. There was dramatic increase in response of the Panc I cells at a p53 DNA concentration of 0.08 μg DNA/well (FIG. 6B). Here an almost 200 fold increase in sensitization was observed. For FIG. 6B, the $IC_{50}$ values were as follows: cys-TfRscFvLipA-p53: 1.8 nM; cys-TfRscFvLipA-Vec: 350 nM; and cys-TfRscFvLipA: 600 nM. The $IC_{50}$ of cys-TfRscFvLipA-Vec/$IC_{50}$ of cys-TfRscFvLipA-p53=194.44. Therefore, these in vitro studies demonstrate that the cys-TfRscFv-liposome, prepared by simple mixing, can efficiently transfect wtp53 into prostate tumor cells and sensitize them to conventional chemotherapeutic agents.

Example 4

In Vivo Tumor Targeting by the cys-TfRscFv-LipA-EGFP Prepared by Simple Mixing

Figure 7A:
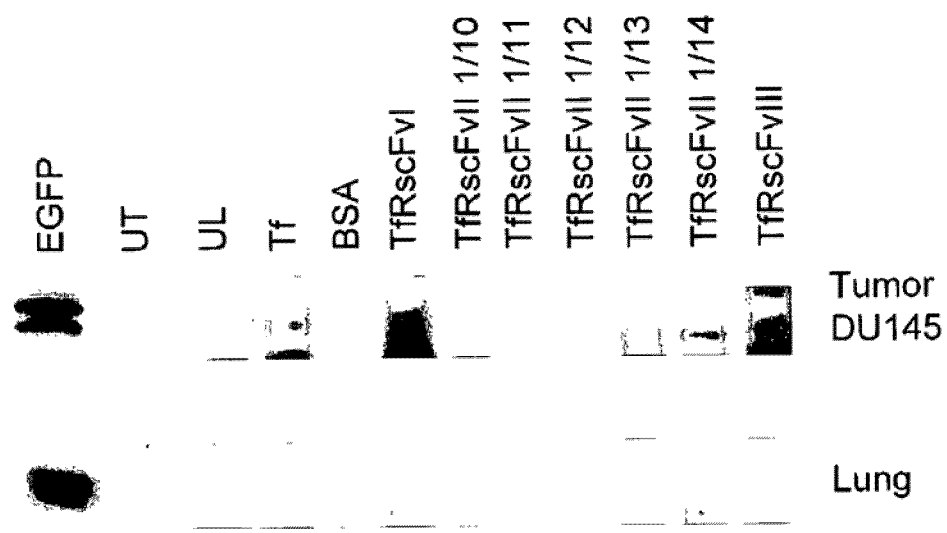
FIG. 7A shows the in vitro tumor targeting ability of the systemically administered TfRscFv-liposome-EGFP complex prepared by simple mixing at various ratios of DNA:lipid

DU145 tumors were subcutaneously induced in female athymic nude (NCR nu/nu) mice. Mice were I.V. tail vein injected three times over a 24 hour period with cys-TfRscFv-LipA-EGFP (enhanced green fluorescence protein) (TfRscFvII) prepared by simple mixing at a scFv:Liposome ratio of 1/30 but at various DNA:total lipid ratios (1/10, 1/11, 1/12, 1/13, 1/14) at 32 ug DNA/injection. For comparison, a complex at 1/30, 1/14 made via the conjugation method (TfRscFv III in FIG. 7B) and a different batch of single chain at 1/30, 1/14 (TfRscFv I in FIG. 7B) also were injected into mice. 60 hours post injection the mice were sacrificed, tumor and lung harvested and protein isolated for Western Blot Analysis using an anti-EGFP antibody. Unliganded LipA-EGFP complex (UL), Tf-LipA-EGFP complex (Tf) and BSA-LipA-EGFP complex (BSA) were injected into mice as controls. FIG. 7A. As shown in the DU145 tumor an EGFP band is observed in the positive controls Tf, TfRscFvIII, and in TfRscFvI. More significantly, a strong EGFP signal was found in TfRscFvII at the DNA to lipid ratio of 1/14. In contrast only very low level of EGFP expression was evident in normal lung tissue. Therefore, the cys-TfRscFv-Lipoplex prepared by simple mixing can target tumor effectively after systemic administration.

Figure 7B:
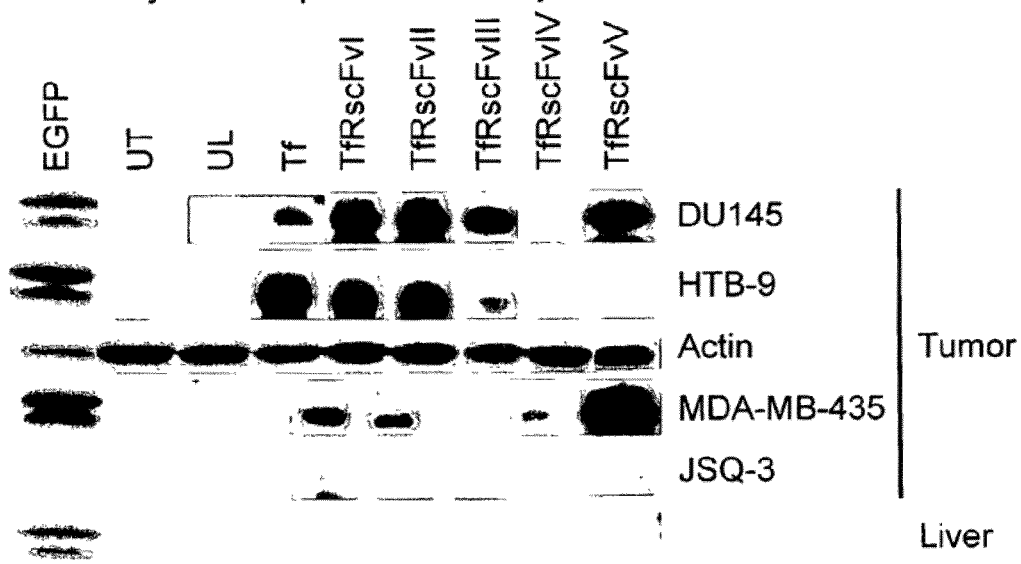
FIG. 7B shows the in vivo tumor targeting ability of the systemically administered TfRscFv-liposome-EGFP complex prepared by simple mixing in four different tumors and using multiple batches of the TfRscFv protein.

To assess the reproducibility of the mixing, different batches of cys-TfRscFv (I to V) were complexed to Liposome A-EGFP by simple mixing at the preferred ratio of 1:30 (scFv:liposome w:w) and 1:14 (μg DNA:n moles total lipid). Human prostate DU145, bladder HTB-9, breast MDA-MB-435 and head and neck JSQ-3 xenograft tumors were subcutaneously induced as above. The complexes also were I.V. tail vein injected three times over a 24 hour period. Tf-LipA-EGFP(Tf) and unliganded LipA-EGFP complex (UL) were used as controls. 60 hours after injection the mice were sacrificed and the tumor and liver were harvested and analyzed as above. Targeting is evident with all of the mixed complexes in the four tumor types (FIG. 7B). However, there is almost no signal in normal tissue (liver). The identical membrane was probed for Actin levels to show equal loading.

Example 5

Figure 8:
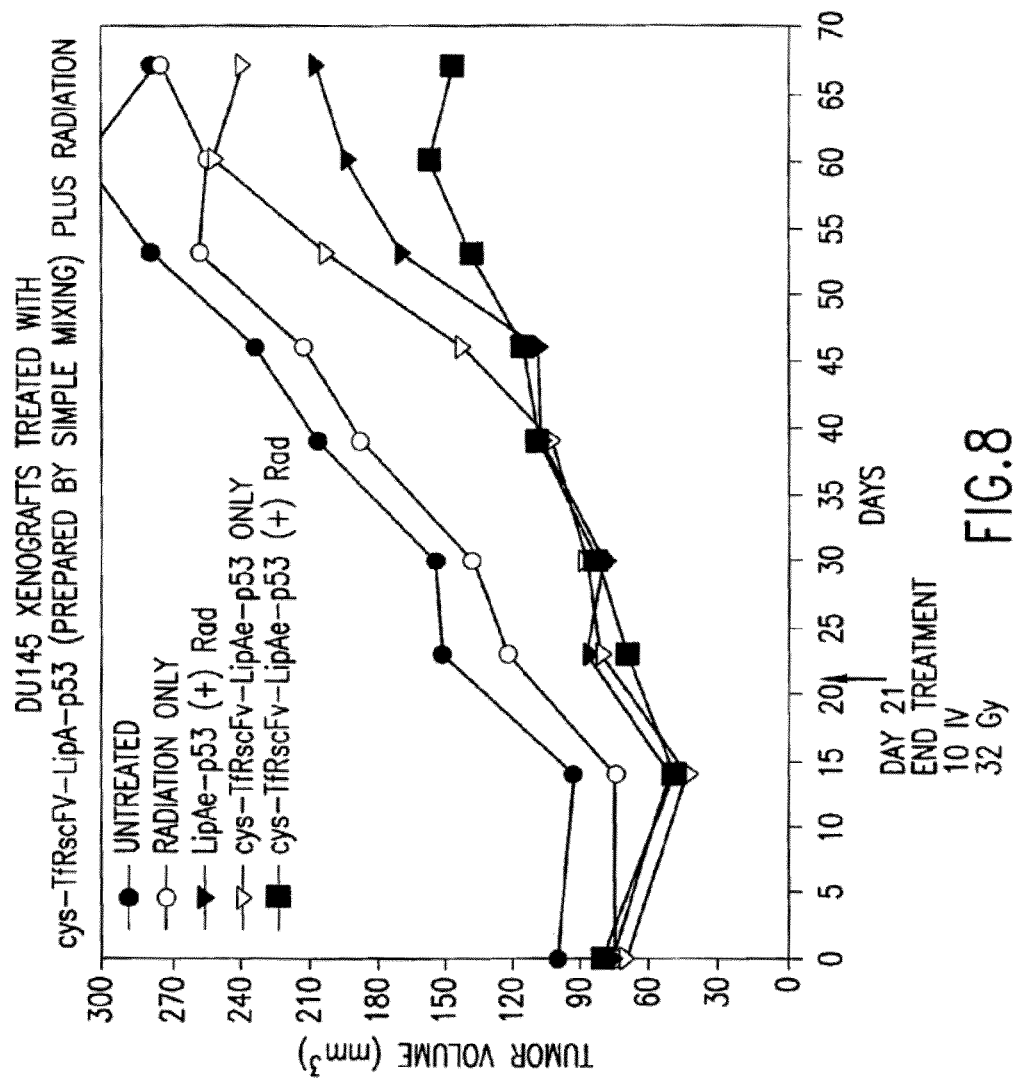
FIG. 8 shows the effect of the combination of systemically administered TfRscFv-liposome A-p53 prepared by simple mixing and radiation on DU145 human prostate xenograft tumors.

Radio/Chemosensitization of Human Xenograft Tumors by Systemically Administered cys-TfRscFv-Liposome-p53 Prepared by Simple Mixing Efficacy studies were performed to further confirm the ability of the cys-TfRscFv-immunoliposome complex of this invention to bind and deliver wtp53 efficiently to tumor cells in vivo. Mice bearing subcutaneous DU145 tumors of approximately 60-90 mm$^3$ were injected, via the tail vein, three times a week (a total of 10 injections) with cys-TfR-scFv-Liposome-p53. This complex was prepared by simple mixing at a ratio of 1/30 (cys-TfRscFv:Liposome A, w:w) and 1/14 (µg DNA/nmoles total lipid). The tumor area was selectively exposed to 2.0 Gy daily fractionated doses of γ-radiation to a total of 32 Gy (FIG. 8). The animals treated with the mixed cys-TFRscFv-liposome A complex plus radiation had significant tumor growth inhibition. Similar findings also were observed using the combination of the anticancer drug GEMZAR® (gemcitabine HCl) and the cys-TFRscFv-immunoliposome of this invention delivering tumor suppressor gene Rb94 to a human bladder carcinoma xenograft tumor (HTB-9), and in Panc I xenografts treated with GEMZAR® (gemcitabine HCl) and cys-TFRscFv-Liposome carrying either another gene inducing apoptosis (Apoptin) or p53.

These findings demonstrate that a complex made by the method of this invention can comprise a variety of genes (incorporated into plasmid vectors) for effective delivery in vivo to cancer cells as a therapeutic treatment.

Example 6

Figure 9:
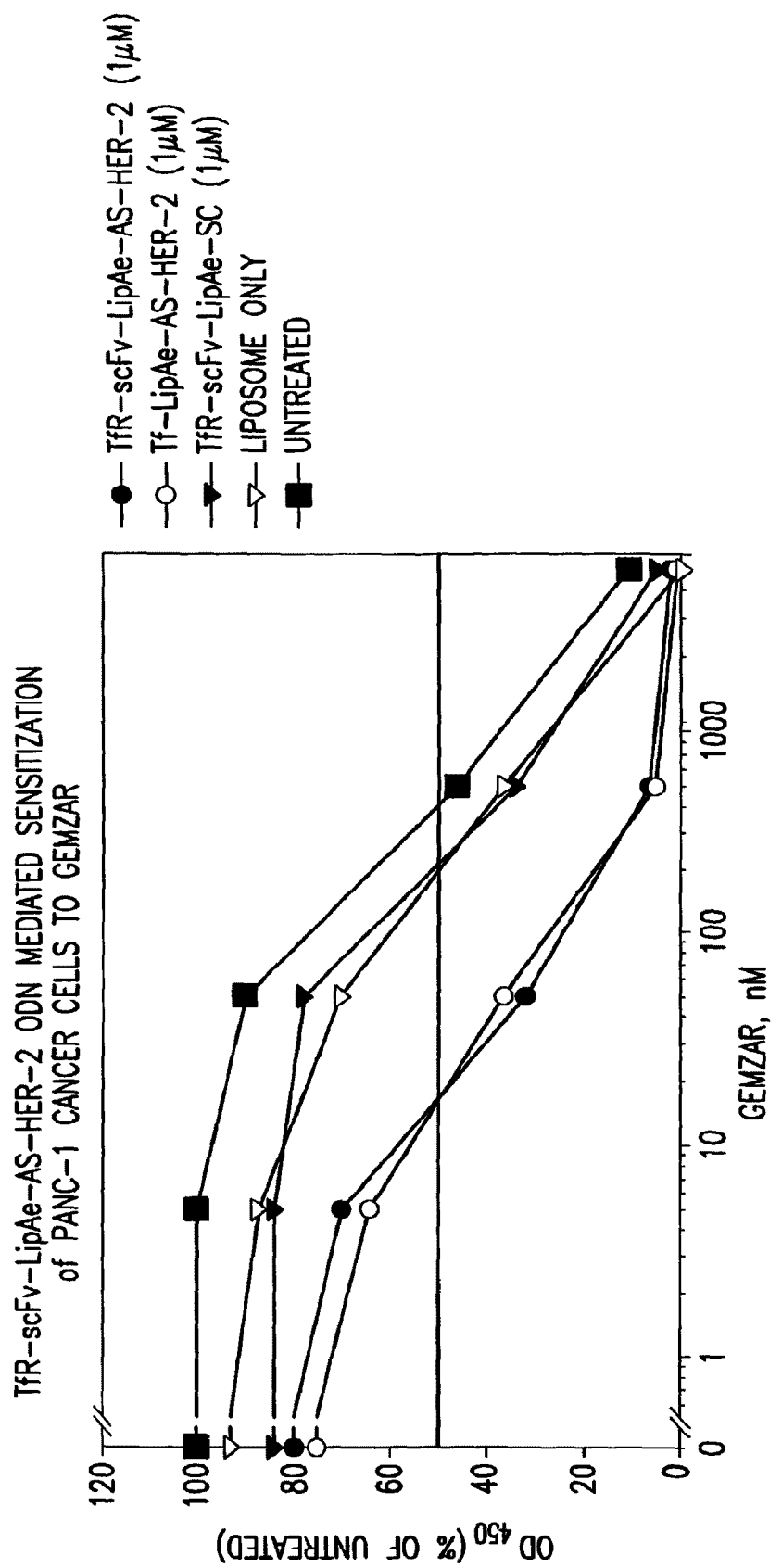
FIG. 9 shows the results of an XTT cytotoxicity assay showing chemosensitivity to gemcitabine HCl (GEMZAR®) induced Panc I cells treated with TfRscFv-liposome-AS HER-2 ODN.

Chemosensitization of Pancreatic Cancer Cells in Vitro by Antisense HER-2 Oligonucleotides Delivered by cys-TFRscFv-Liposome A Prepared by Simple Mixing This example demonstrates the usefulness of this invention in efficiently delivering molecules other than genes to tumor cells for therapeutic treatment. The complex was prepared as in Example 2, however, the DNA encapsulated here was an 18 mer phosphorothioated oligonucleotide (ODN) directed against the initiation codon of the HER-2 gene (AS HER-2) (51). The ratio used was as above for plasmid DNA 1:30 (cys-TfRscFv:liposome, w:w) and 1:14 (n moles ODN:n mole total lipids). Panc I cells, at 4×10$^3$ cells/well, were seeded in a 96 well plate. The cells were transfected 24 hours later by cys-TfRscFv-LipA-AS HER-2 prepared by the method of this invention. Tf-LipA-AS HER-2 and cys-TfR-scFv-LipA-SC ODN were used as controls. SC ODN is a scrambled ODN that has the same nucleotide composition as the AS HER-2 ODN but in random order. As shown in FIG. 9 the cys-TfRscFv-Lip A-AS HER-2 complex prepared by the method of this invention was able to sensitize pancreatic cancer cell line Panc I to the effects of chemotherapeutic agent GEMZAR® (gemcitabine HCl) by over 11 fold. This increase in sensitization is identical to that resulting from transfection with the positive control Tf-LipA-AS HER2 complex. For FIG. 9, the IC$_{50}$ values were as follows: TfR-scFv-LipA3-AS-HER-2: 16 nM; Tf-LipAe-AS-HER-2: 14 nM and TfR-scFv-LipAe-SC: 200 nM. The IC$_{50}$ of TfR-scFv-LipAe-SC/IC$_{50}$ of TfR-scFv-LipAe-AS-HER-2-12.5.

Example 7

Figure 10A:
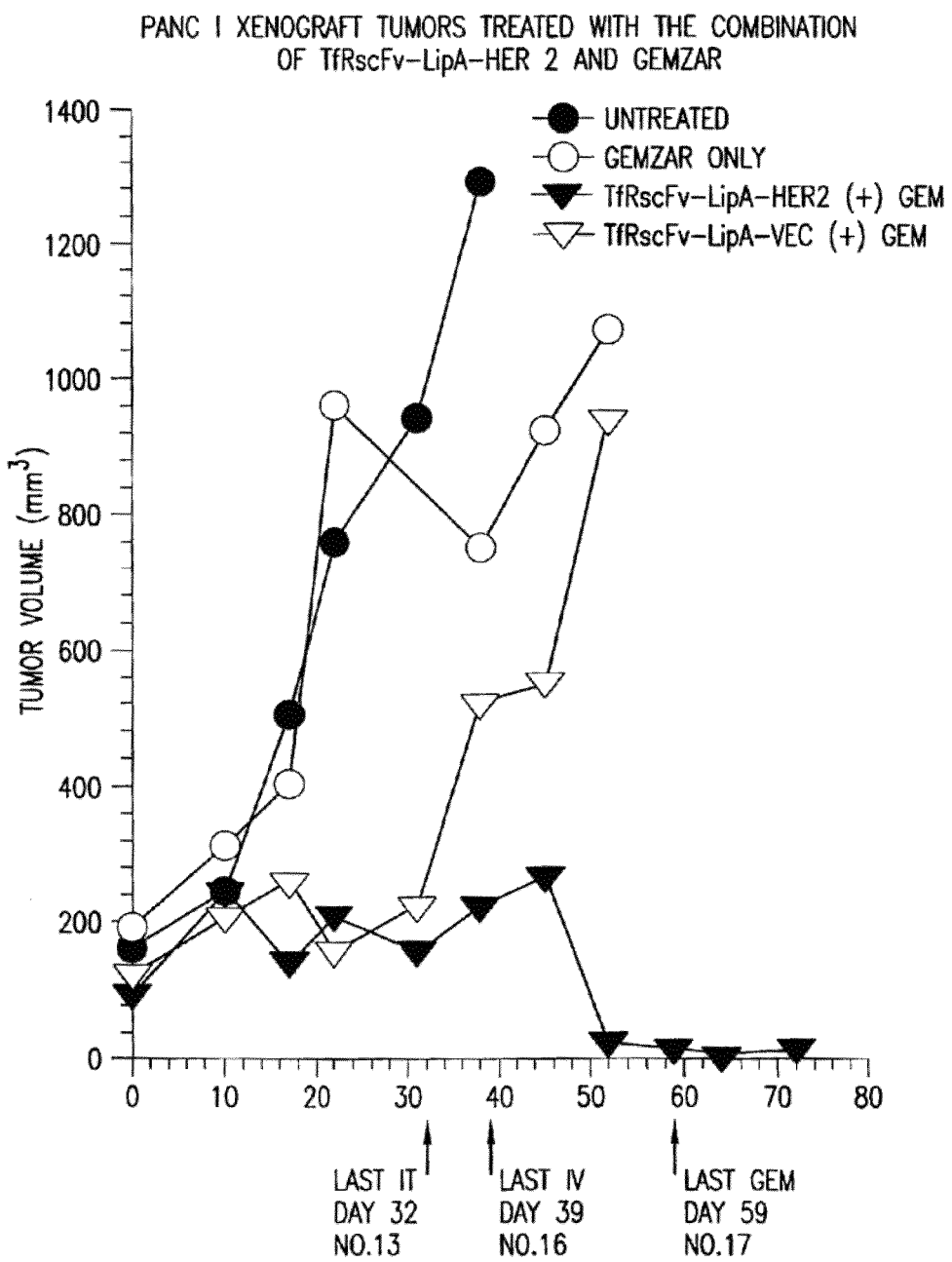
FIG. 10A shows the effect of the combination of systemically administered TfRscFv-liposome A-AS HER-2 ODN and gemcitabine HCl (GEMZAR®) on Panc I human pancreatic xenograft tumors.

In Vivo Chemosensitization of Human Xenograft Tumors by Systemically Delivered cys-TFRscFv-LipA-AS HER-2 ODN Prepared by Simple Mixing In this example, the ability of the cys-TfRscFv liposome-DNA complex prepared by the method of this invention to deliver an antisense molecule to tumor cells in vivo after systemic delivery is demonstrated. To show the universality of this delivery system two different human xenograft mouse tumor models (pancreatic cancer and breast cancer) were employed. In the first (FIG. 10A) Panc I subcutaneous xenograft tumors were induced in female athymic nude (NCR nu/nu) mice. When the tumors were 100-200 mm$^3$ in size the animals were injected with the chemotherapeutic agent GEMZAR® (gemcitabine HCl) (intraperitoneally) and with cys-TfRscFv-LipA AS HER-2 prepared by the method of this invention (I.V.). The complex was made using the ratio of 1:30 (cys-TfRscFv:liposome, w:w) and 1:15 (n mole ODN:n mole total lipid). In addition to the I.V. injections the complex described above also was intratumorally injected. One group of animals received GEMZAR® (gemcitabine HCl) only and a second control group received GEMZAR® (gemcitabine HCl) plus the complex carrying empty vector. Treatment with GEMZAR® (gemcitabine HCl) alone was not able to significantly inhibit pancreatic tumor growth. In contrast (FIG. 10A), the combination of GEMZAR® (gemcitabine HCl) and AS-HER-2 ODN delivered by the cys-TfRscFv-Lip A complex prepared by the method of this invention not only significantly inhibited tumor growth but also resulted in tumor regression.

Figure 10B:
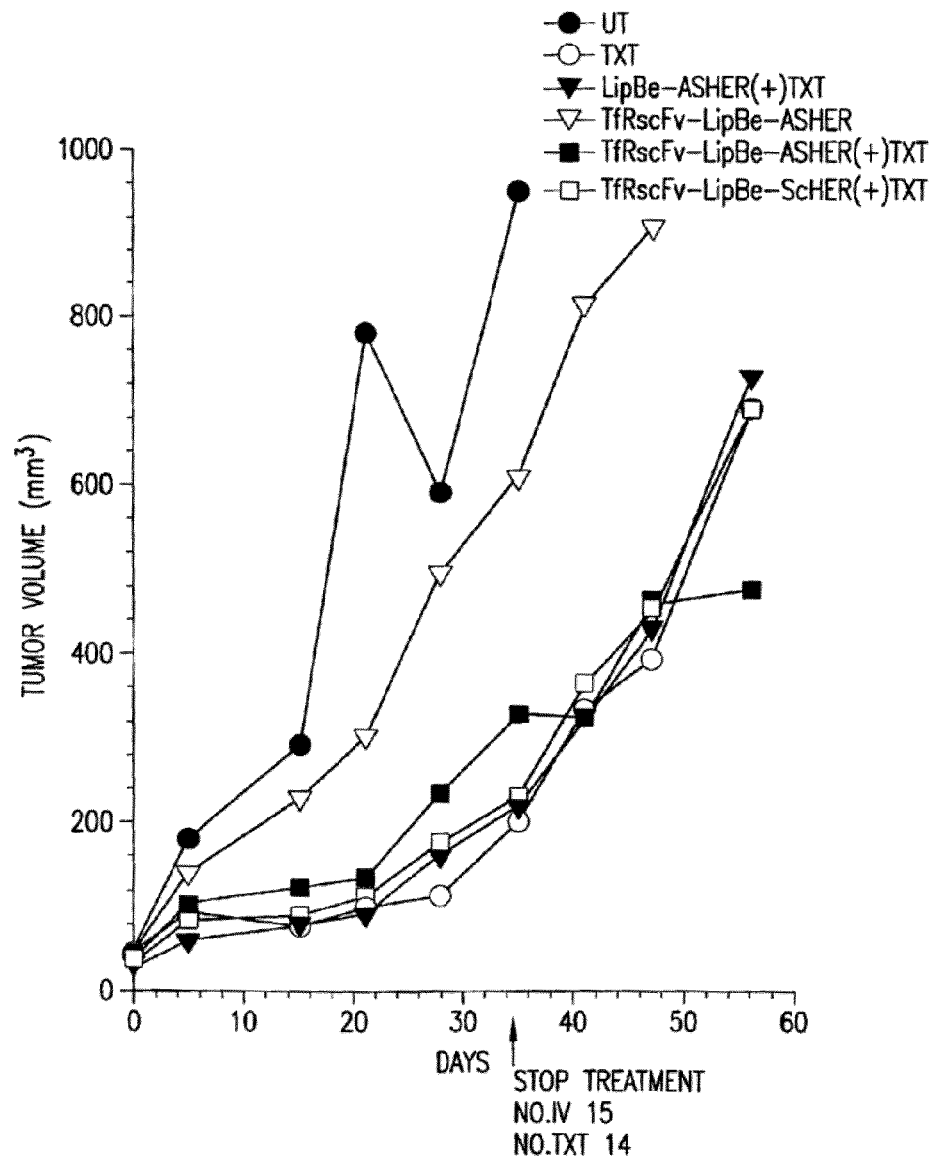
FIG. 10B shows the effect of the combination of systemically administered TfRscFv-liposome B-AS HER-2 ODN and docetaxel (TAXOTERE®) on MDA-MB-435 human breast xenograft tumors.

Significant tumor growth inhibition of human breast cancer xenograft tumors also was observed with the combination of the drug TAXOTERE® (docetaxel; manufactured by Aventis Pharmaceuticals, Collegeville, Pa.) and I.V. administered cys-TfRscFv-LipB AS HER-2 prepared by the method of this invention (FIG. 10B). While liposome formulation B was used in the breast tumor, the same ratios as described above for Panc I were employed.

Example 8

Enhancement of MRI Image by Delivery of Imaging Agent Magnivest® by cys-TFRscFv-Liposome A prepared by Simple Mixing This example demonstrates the ability to encapsulate MRI imaging agents and form a cys-TfRscFv-Liposome-imaging agent complex by the method of this invention. The complex prepared by the method of this invention can be administered intravenously resulting in increased enhancement of the tumor image. These imaging agents can include, but are not limited to, MAGNEVIST® (Gd-DTPA) (Schering AG). The ratios used to form the complex by simple mixing are the preferred ratios of 1:30 (cys-TfRscFv:liposome, w:w) and 1:14 (ug imaging agent nmoles lipid). In these studies 16 ul of MAGNEVIST® (Gd-DTPA) were used in the complex.

Figure 11:
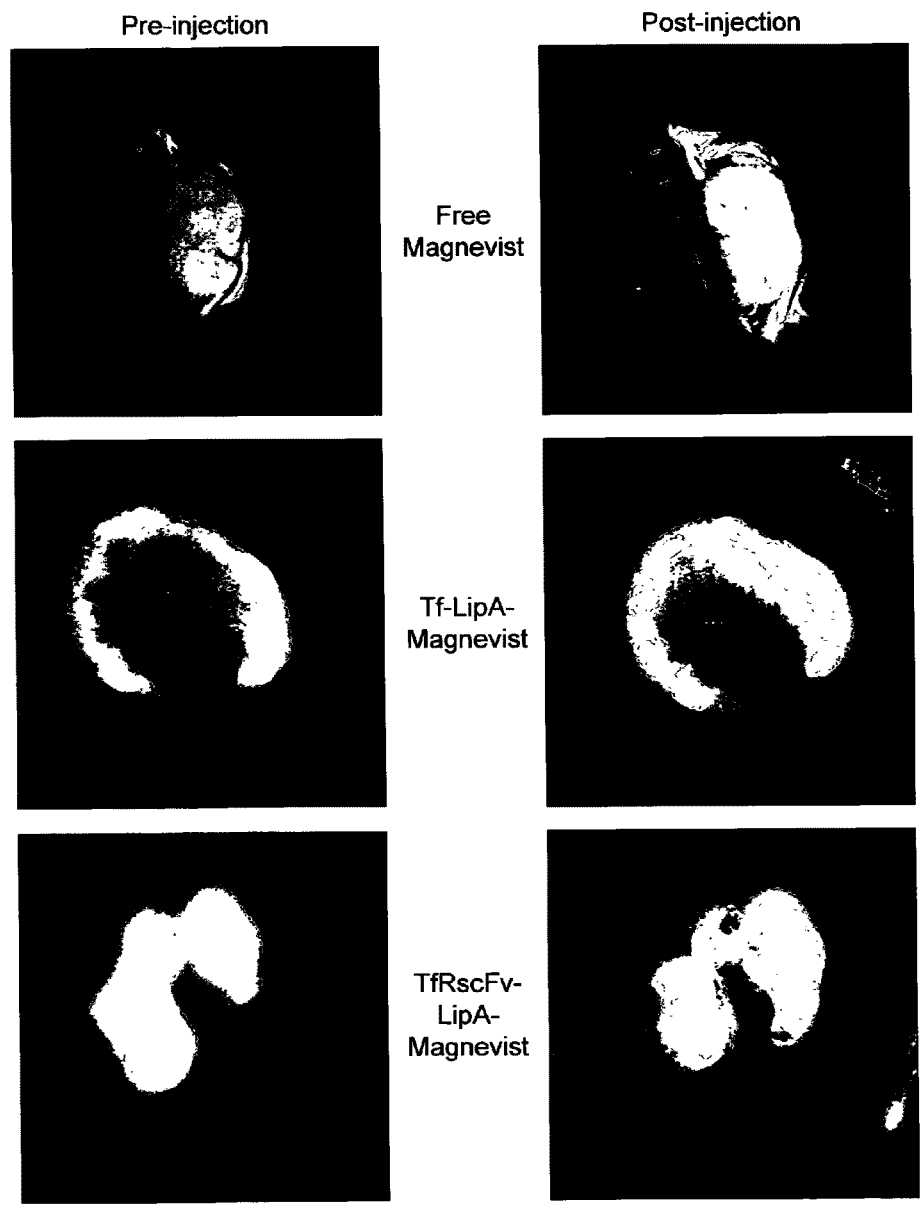
FIG. 11 shows the enhanced tumor imaging resulting from the systemic administration of the TfRscFv-liposome-MAG-NEVIST® (Gd-DTPA) complex.

FIG. 11 shows the results from one I.V. injection of the cys-TfRscFv-LipA-MAGNEVIST® (Gd-DTPA) made by the method of this invention into mice bearing subcutaneous xenograft tumors of human head and neck (top panel), breast (middle panel) or prostate (bottom panel) origin. A higher level of imaging agent enhancement is evident in the tumor that received the cys-TfRscFv-LipA-MAGNEVIST® (Gd-DTPA) as compared to that receiving free MAGNEVIST® (Gd-DTPA) demonstrating the benefit of administering the imaging agent using the complex prepared by the method of this invention. In other experiments an increased uptake in the tumor as compared to the surrounding normal tissue also was observed.

Similar enhancement also was observed using syngenetic mouse lung metastasis model. $B_{16}/F_{10}$ mouse melanoma cells were injected intravenously into C57BL/6 mice. These cells form tumor nodules in the mouse lungs. The cys-TfRscFv-Liposome-MAGNEVIST® (Gd-DTPA) complex was prepared by the method of this invention also using the preferred ratios of 1:30 and 1:14. The complex was I.V. administered and the tumor modules imaged via MRI. Compared to free MAGNEVIST® (Gd-DTPA), the encapsulated imaging agent also has a prolonged uptake in the tumor since the peak enhancement with the complex is later than that of the free MAGNEVIST® (Gd-DTPA).

Example 9

Preparation of Sterically Stabilized Immunoliposomes by Simple Mixing

Liposomal complexes are rapidly cleared from the blood stream by the reticuloendothelial system. In an effort to prolong this circulation time sterically stabilized liposomes have been formulated that have a hydrophilic polymer such as PEG integrated into the liposome complex. Various methods have been devised to include a targeting ligand such as an antibody or antibody fragment in the PEG-liposome complex. Most, if not all, of these methodologies involve a chemical conjugation step to link the antibody or antibody fragment to the PEG. Such harsh chemical reactions and the method used to form the complex can result in loss or masking of antibody activity. In this example, we demonstrate that the cys-TfRscFv protein can be linked to a PEG-liposome molecule by simple mixing and that the resultant complex can more efficiently transfect human tumor cells.

To form this complex, a lipoplex consisting of one of the cationic lipid formulations given in Example 2 was mixed with nucleic acid at a ratio of 1:14 (ug DNA:n moles lipid) as described in Example 2. To this lipoplex was added the commercially available NHS-PEG-MAL polymer (2%) in 25 mM HEPE Buffer (pH 7.2). The solution was gently inverted for 3-5 seconds and incubated at room temperature for 1.5 hours. To form the cys-TfRscFv-PEG-Liposome-DNA complex, the cys-TfRscFv protein was added to the PEG-lipoplex at a ratio of 1:8 (cys-TfRscFv:liposome, w:w), inverted gently and kept at room temperature for 10 minutes to 1 hour, then used to transfect the cells in vitro. Other ratios in the range of 1:5 to 1:30 (cys-TfRscFv:liposome, w:w) could also be employed to form the complex. For in vivo use, 50% Dextrose was added to a final concentration of 5% after the incubation, mixed gently by inversion and injected into animals. Alternatively, the final complex could have been stored at 4° C. overnight (12-18 hr).

In the experiment shown here the nucleic acid was pLuc, a plasmid DNA that codes for the firefly luciferase gene. Human breast cancer cells MDA-MB-435 were plated at $5 \times 10^4$ cells/well. Twenty-four hours later they were transfected with the cys-TfRscFv-PEG-LipA-pLuc as described in Example 3 and the transfection efficiency assessed by the level of luciferase activity. As shown in FIG. 12 the cys-TfRscFv-PEG-LipA-pLuc complex prepared by the method of this invention was able to transfect the target cells with better efficiency than the PEG-LipA-pLuc without the targeting cys-TfRscF protein.

Thus the method of simple mixing described here also can be used as a simple, non-destructive means of preparing sterically stabilized targeted immunoliposomes.

LITERATURE CITED

1. Felgner, P. L., Tsai Y. J., Sukhu, L., Wheeler, C. J., Manthorpe M., Marshall, J. and Cheng S. H., *Ann NY Acad. Sci.,* 772, 126-139 (1995).
2. Lewis, J. G., Lin, K. Y., Kothavale, A., Flanagan, W. M., Matteucci, M. D., DePrince, R. B., Mook, R. A., Hendren, R. W., and Wagner, R. W., *Proc. Natl. Acad. Sci USA,* 93, 3176-3181 (1996).
3. Aoki, K., Yoshida, T., Sugimura, T. and Terada, *Cancer Res.,* 55, 3810-3816 (1997).
4. Clark, P. R., Hersh, E. M., *Curr. Opin Mol. Ther,* 1, 158-176 (1999).
5. Thierry, A. R., Lunardi-Iskandar, Y., Bryant, J. L., Rabinovich, P., Gallo, R. C. and Mahan, L. C., *Proc Natl. Acad Sci,* 92, 9742-9746 (1997).
6. The Journal of Gene Medicine Clinical Trials Database, http://www.wiley.co.uk/wileychi/genmed/clinical, September, (2001).
7. Cristiano, R. J. and Curiel, D. T., *Cancer Gene Ther,* 3(1), 49-57 (1996).
8. Cheng, P. W., *Hum Gene Ther,* 7, 275-282 (1996).
9. Keer, H. N., Kozlowski, J. M. and Tsai, M. C., *J. Urol* 143, 381-385 (1990).
10. Chackal-Roy, M., Niemeyer, C and Moore, M., *J. Clin. Invest.,* 84, 43-50 (1989).
11. Rossi, M. C. and Zetter, B. R., *PNAS,* 89, 6197-6201 (1992).
12. Grayhack, J. T., Wendel, E. F. and Oliver, L., *J. Urol.* 121, 295-299 (1979).
13. Elliott, R. L., Elliott, M. C., Wang, F. and Head, J. F., *Ann NY Acad Sci,* 698, 159-166 (1993).
14. Miyamoto, T., Tanaka, N., Eishi, Y. and Amagasa, T., *Int. J. Oral Maxillofac Surg* 23, 430-433 (1994).
15. Thorstensen, K. and Romslo, I., *Scad J. Clin Lab Invest. Suppl.,* 215, 113-120 (1993).
16. Xu, L., Pirollo, K. F. and Chang, E. H., *Hum Gen Ther,* 8, 467-475 (1997)
17. Xu, L., Pirollo, K. F., Tang, W-H., Rait, A., and Chang, E. H., *Human Gene Therapy,* 10, 2941-2952 (1999).
18. Xu, L., Frederik, P., Pirollo, K. F., Tang, W-H, Rait, A., Xiang, L-M, Huang, W., Cruz, I., Yin, Y. and Chang, E. H., *Human Gene Therapy,* 13, 1-13 (2002).
19. Allen, T. M., Hansen, C. B. & Zalipsky, S., *Stealth Liposomes,* 233-44 (1995).
20. Allen, T. M., *Biochim Biophys Acta,* 1237, 99-108 (1995).
21. Lasic, D. D., Vallner, J. J. and Working, P. K., *Current Opinions in Molecular Therapeutics,* 1, 177-185 (1999).
22. Park, J. W., Hong, K., Carter, P., Asgari, H., Guo, L. Y., Keller, G. A., Wirth, C., Shalaby, R., Kotts, C., Wood, W. I., Papahadjopoulos, D and Benz, C. C., *Proc. Natl. Acad. Sci USA,* 92, 1327-1331 (1995).
23. Park, J. W., Kirpotin, D. B., Hong, K., Shalaby, R., Shao, Y., Nielson, U. B., Marks, J. D., Papahadjopoulos, D., Benz, C. C., *J. Control Release,* 74 (1-3), 95-113 (2001).

24. Koning, G. A., Gorter, A., Scherphof, G. L. and Kamps, J. A., *British Journal of Cancer,* 80, 1718-1725 (1999).
25. Koning, G. A., Morselt, H. W., Velinova, M. J., Donga, J., Gorter, A., Allen, T. M., Zalipsky, S., Kamps, J. A. and Scherphof, G. L., *Biochemica et Biophysica Acta,* 1420, 153-167 (1999).
26. Nam, S. M., Kim, H. S., Ahn, W. S. and Park, Y. S., *Oncology Research* 11, 9-16 (1999).
27. Pagnan, G., Montaldo, P. G., Pastorino, F., Raffaghello, L., Kirchmeier, M., Allen, T. M. and Ponzoni, M., *International Journal of Cancer,* 81, 268-274 (1999).
28. Ng, K., Zhao, L., Liu, Y and Mahapatro, M., *International Journal of Pharmaceutics,* 193, 157-166 (2000).
29. Pirollo, K. F., Xu, L., Chang, E. H., Immunoliposomes: a targeted delivery tool for cancer treatment. In: *Vector Targeting for Therapeutic Gene Delivery,* D. Curiel (Ed.); Wiley Press (2002) In Press
30. Poon, R. Y., in *Biotechnology International: International Developments in the Biotechnology Industry* (eds. Fox F and Connor, T. H.) 113-128 (Universal Medical Press, Inc., San Francisco, Calif., 1997).
31. Weinberg, E. D., *Biol. Trace Elements Res.,* 34, 123-140 (1992).
32. Reviews: p. 53. In: *Oncogene Reviews.* Jenkins, J. R., Banks L. M. (Eds), Stockton Press, London (1999): 18, 7617-777.
33. Sidransky, D., Hollstein, M., *Annual Review of Medicine,* 1996, 47, 285-301.
34. Ruley, H. E., In: *Important Advances in Oncology* 1996. Edited by DeVita, V. T., Hellman, S and S. A. Rosenberg, Philadelphia: Lippincott-Raven Publishers; 1996: 37-56.
35. Bristow, R. G., Benchimol, S., Hill, R. P.,: *Radiotherapy & Oncology,* 40, 1996, 197-223.
36. Chiarugi, V., Magnelli, L., Gallo, O., *Int. J. Mol. Med.,* 2, 715-719, 1998.
37. Volpert, O. V., Dameron, K. M., Bouck, N., *Oncogene,* 1997, 14, 1495-1502.
38. Kerr, J. F., Winterford, C. M. and Harmon, B. V., *Cancer,* 73, 1994, pp. 2013-2026.
39. Lowe, S. W., *Curr. Opin Oncol.,* 7, 547-553 (1995).
40. Johnson, P., Gray, D., Mowat, M. and Benchimol, J. S., *Mol. Cell Biol.,* 11, 1-11 (1991).
41. Yang, C., Cirielli, C., Capogrossi, M. C. and Passaniti, A., *Cancer Res.,* 55, 4210-4213 (1995).
42. Srivastava, S., Katayose, D., Tong, Y. A., Craig, C. R., McLeod, D. G., Moul, J. W., Cowan, K. H. and Seth, P., *Urology,* 46, 843-848 (1995).
43. Pirollo, K. F., Zhengmei, H., Rait, A., Jang, Y. J., Fee, W. E., Ray, P., Chiang, Y. and Chang, E. H., *Oncogene,* 14, 1735-1746 (1997).
44. Liu, T. J., Zhang, W. W., Taylor, D. L., Roth, J. A., Goepfert, H. and Clayman, G. L., *Cancer Res.,* 54, 3662-3667 (1994).
45. Miyashita, T., Krajewski, S., Krajewska, M., Wang, H. G., Lin, H. K., Liebermann, D. A., Hoffman, B. & Reed, J. C., *Oncogene,* 9(6), 1799-1805 (1994).
46. Hamada, K., Alemany, R., Zhang, W. W., Hittelman, W. N., Lotan, R., Roth, J. A. and Mitchell, M. F., *Cancer Res.,* 56 (3), 3047-3054 (1996).
47. Fujiwara, T., Grimm, E. A., Mukhopadhyay, T., Zhang, W. W., Owen-Schaub, L. B. and Roth, J. A., *Cancer Res,* 54, 2287-2291 (1994).
48. Fujiwara, T., Grimm, E. A., Mukhopadhyay, T., Cai, D. W., Owen-Schaub, L. B. and Roth, J. A., *Cancer Res,* 53, 4129-4133 (1993).
49. Xu, L., Pirollo, K. F., Rait, A., Murray, A. L. and Chang, D. H., *Tumor Targeting,* 4, 92-104 (1999).
50. Xu, L., Pirollo, K. F., Tang, W., Rait, A. and Chang, E. H., *Human Gene Therapy,* 10, 2941-2952 (1999),
51. Rait, A., Pirollo, K., Rait, V., Krkygier, J., Xiang, L. and Chang, E. H., *Cancer Gene Therapy* 8, 728-739 (2001).
52. Yazdi, P. T., Wenning, L. A. and Murphy, R. M., *Cancer Res.,* 55, 3763-3771 (1995).
53. Dube'D, Francis, M., Leroux J-C and Winnik, F. M., *Bioconjugate Chemistry* 10, On line article, 2002.

What is claimed is:

1. An antibody- or antibody fragment-targeted cationic immunoliposome complex comprising:
   a) an antibody or antibody fragment;
   b) a cationic liposome, wherein said antibody or antibody fragment is complexed with said cationic liposome, but is not chemically conjugated to said cationic liposome, and wherein said antibody or antibody fragment does not comprise a lipid tag; and
   c) an agent selected from the group consiting of a therapeutic agent, a diagnostic agent and a reporter gene, wherein said immunoliposome complex is 50-400 nm in size.

2. The targeted cationic immunoliposome complex of claim 1, comprising an antibody.

3. The targeted cationic immunoliposome complex of claim 1, comprising an antibody fragment.

4. The targeted cationic immunoliposome complex of claim 1, wherein said antibody fragment is a single chain Fv fragment.

5. The targeted cationic immunoliposome complex of claim 1, wherein said antibody fragment is an anti-transferrin receptor single chain Fv (TfRscFv).

6. The targeted cationic immunoliposome complex of claim 1, wherein said antibody or antibody fragment is an anti-HER-2 antibody or antibody fragment.

7. The targeted cationic immunoliposome complex of claim 1, wherein said cationic liposome comprises a mixture of one or more cationic lipids and one or more neutral or helper lipids.

8. The targeted cationic immunoliposome complex of claim 1, wherein said cationic liposome comprises a mixture of dioleoyltrimethylaminonium phosphate with dioleoylphosphatidylethanolamine and/or cholesterol, a mixture of dioleoyltrimethylammonium phosphate with dioleoylphosphatidylethanolamine, a mixture of dimethyldioctadecylammmonium bromide with dioleoylphosphatidylethanolamine; or a mixture of dimethyldioctadecylammonium bromide with dioleoylphosphatidylethanolamine and/or cholesterol.

9. The targeted cationic immunoliposome complex of claim 1, wherein said agent is a therapeutic agent and comprises plasmid DNA or a nucleic acid molecule.

10. The targeted cationic immunoliposome complex of claim 9, wherein said nucleic acid molecule encodes a tumor suppressor protein.

11. The targeted cationic immunoliposome complex of claim 10, wherein said tumor suppressor protein is p53, Rb94 or Apoptin.

12. The targeted cationic immunoliposome complex of claim 1, wherein said agent is a diagnostic agent.

13. The targeted cationic immunoliposome complex of claim 1, formulated as a pharmaceutically acceptable formulation for in vivo administration.

14. The targeted cationic immunoliposome complex of claim 13, further comprising a pharmacologically acceptable carrier.

15. The targeted cationic immunoliposome complex of claim 13, wherein said complex is formulated for intravenous administration, intratumoral administration, intralesional administration, aerosol administration, percutaneous administration, endoscopical administration, topical administration or subcutaneous administration.

16. The targeted cationic immunoliposome complex of claim 13, wherein said complex is formulated for intravenous administration.

17. The targeted cationic immunoliposome complex of claim 1, wherein said complex targets tumor cells.

18. The targeted cationic immunoliposome complex of claim 1, wherein said complex targets non-tumor cells.

19. The targeted cationic immunoliposome complex of claim 18, wherein said non-tumor cell is a dendritic cell, an endothelial cell, a lung cell, a breast cell, or a liver cell.

20. A targeted cationic immunoliposome complex comprising:
   a) an anti-transferrin receptor single chain Fv (TfRscFv);
   b) a cationic liposome comprising a mixture of dioleoyltrimethylammonium phosphate with dioleoylphosphatidylethanolamine, wherein said TfRscFv is complexed with said cationic liposome, but is not chemically conjugated to said cationic liposome, and wherein said TfRscFv does not comprise a lipid tag; and
   c) a nucleic acid molecule encoding a tumor suppressor protein, wherein said antibody- or antibody fragment-targeted cationic immunoliposome complex is 50-400 nm in size.

21. The targeted cationic immunoliposome complex of claim 20, wherein said tumor suppressor protein is p53, Rb94 or Apoptin.

22. An antibody- or antibody fragment-targeted cationic immunoliposome complex prepared by a process comprising:
   a) preparing an antibody or antibody fragment;
   b) mixing said antibody or antibody fragment with a cationic liposome to form a cationic immunoliposome, wherein said antibody or antibody fragment is complexed with said cationic liposome, but is not chemically conjugated to said cationic liposome, and wherein said antibody or antibody fragment does not comprise a lipid tag; and
   c) mixing said cationic immunoliposome with an agent selected from the group consisting of a therapeutic agent, a diagnostic agent, and a reporter gene to form said antibody- or antibody fragment-targeted cationic immunoliposome complex,
wherein said antibody- or antibody fragment-targeted cationic immunoliposome complex is 50-400 nm in size.

23. The targeted cationic immunoliposome complex of claim 22, wherein said antibody is mixed with said cationic liposome.

24. The targeted cationic immunoliposome complex of claim 22, wherein said antibody fragment is mixed with said cationic liposome.

25. The targeted cationic immunoliposome complex of claim 22, wherein said antibody fragment is a single chain Fv fragment.

26. The targeted cationic immunoliposome complex of claim 22, wherein said antibody fragment is an anti-transferrin receptor single chain Fv (TfRscfv).

27. The targeted cationic immunoliposome complex of claim 22, wherein said antibody or antibody fragment is an anti-HER-2 antibody or antibody fragment.

28. The targeted cationic immunoliposome complex of claim 22, wherein said antibody fragment comprises a cysteine moiety at a carboxy terminus prior to being mixed with said cationic liposome.

29. The targeted cationic immunoliposome complex of claim 22, wherein said cationic liposome comprises a mixture of one or more cationic lipids and one or more neutral or helper lipids.

30. The targeted cationic immunoliposome complex of claim 22, wherein said antibody or antibody fragment is mixed with said cationic liposome at a ratio in the range of 1:5 to 1:40 (w:w).

31. The targeted cationic immunoliposome complex of claim 22, wherein said cationic liposome comprises a mixture of dioleoyltrimethylammonium phosphate with dioleoylphosphatidylethanolamine and/or cholesterol, a mixture of dioleoyltrimethylammonium phosphate with dioleoylphosphatidylethanolamine, a mixture of dimethyldioctadecylammonium bromide with dioleoylphosphatidylethanolamine; or a mixture of dimethyldioctadecylammonium bromide with dioleoylphosphatidylethanolamine and/or cholesterol.

32. The targeted cationic immunoliposome complex of claim 22, wherein said antibody or antibody fragment and liposome are mixed with said therapeutic agent, said diagnostic agent, or said reporter gene, at a ratio in the range of 1:8 to 1:20 (µg of agent or reporter gene:nmole of total lipid).

33. The targeted cationic irnmunoliposome complex. of claim 22, wherein said agent is a therapeutic agent and comprises plasmid DNA or a nucleic acid molecule.

34. The targeted cationic immunoliposome complex of claim 33, wherein said a nucleic acid molecule encodes a tumor suppressor protein.

35. The targeted cationic immunoliposome complex of claim 34, wherein said tumor suppressor protein is p53, Rb94 or Apoptin.

36. The targeted cationic immunoliposome complex of claim 22, wherein said agent is a diagnostic agent.

37. The targeted cationic immunoliposome complex of claim 22, wherein said process further comprises formulating said complex as a pharmaceutically acceptable formulation for in vivo administration.

38. The targeted cationic immunoliposome complex of claim 37, wherein said complex is combined with a pharmacologically acceptable carrier.

39. The targeted cationic irumunoliposome complex of claim 37, wherein said complex is formulated for intravenous administration, intraturnoral administration, intralesional administration, aerosol administration, percutaneous administration, endoscopical administration, topical administration or subcutaneous administration.

40. The targeted cationic immunoliposome complex of claim 37, wherein said complex is formulated for intravenous administration.

41. The targeted cationic immunoliposome complex of claim 22, wherein said complex targets tumor cells.

42. The targeted cationic immunoliposome complex of claim 22, wherein said complex targets non-tumor cells.

43. The targeted cationic immunoliposome complex of claim 42, wherein said non tumor cell is a dendritic cell, an endothelial cell, a lung cell, a breast cell, or a liver cell.

44. A method of delivering a therapeutic agent, a diagnostic agent, or a reporter gene to a cell in a mammal, the method comprising administering to said mammal an antibody- or antibody fragment-targeted cationic immunoliposome complex comprising:
   a) an antibody or antibody fragment;
   b) a cationic liposome, wherein said antibody or antibody fragment is complexed with said cationic liposome, but is not chemically conjugated to said cationic liposome, and wherein said antibody or antibody fragment does not comprise a lipid tag; and
   c) an agent selected from the group consisting of a therapeutic agent, a diagnostic agent and a reporter gene wherein said antibody- or antibody fragment-targeted cationic immunoliposome complex is 50-400 nm in size.

45. The method claim 44, wherein said complex comprises an antibody.

46. The method of claim 44, wherein said complex comprises an antibody fragment.

47. The method of claim 44, wherein said antibody fragment is a single chain Fv fragment.

48. The method of claim 44, wherein said antibody fragment is an anti-transferrin receptor single chain Fv (TfR-scFv).

49. The method of claim 44, wherein said antibody or antibody fragment is an anti-HER-2 antibody or antibody fragment.

50. The method of claim 44, wherein said cationic liposome comprises a mixture of one or more cationic lipids and one or more neutral or helper lipids.

51. The method of claim 44, wherein said cationic liposome comprises a mixture of dioleoyltrimethylammonium phosphate with dioleoylphosphatidylethanolamine and/or cholesterol, a mixture of dioleoyltrimethylammonium phosphate with dioleoylphosphatidylethanolamine, a mixture of dimethyldioctadecylammonium bromide with dioleoylphosphatidylethanolamine; or a mixture of dimethyldioctadecylammonium bromide with dioleoylphosphatidylethanolamine and/or cholesterol.

52. The method of claim 44, wherein said agent is a therapeutic agent and comprises plasmid DNA or a nucleic acid molecule.

53. The method of claim 52, wherein said nucleic acid molecule encodes a tumor suppressor protein.

54. The method of claim 53, wherein said tumor suppressor protein is p53, Rb94 or Apoptin.

55. The method of claim 44, wherein said agent is a diagnostic agent.

56. The method of claim 44, wherein said complex is administered intravenously, intratumorally, intralesionally, via aerosol, percutaneously, endoscopically, topically or subcutaneously.

57. The method of claim 44, wherein said complex is administered intravenously.

58. The method of claim 44, wherein said therapeutic. agent, said diagnostic agent or said reporter gene is delivered to a tumor cell.

59. The method of claim 44, wherein said therapeutic agent, said diagnostic agent or said reporter gene is delivered to a non-tumor cell.

60. The method of claim 59, wherein said non-tumor cell is a dendritic cell, an endothelial cell, a lung cell, a breast cell, or a liver cell.

61. The method of claim 44, further comprising administering said complex in combination with another therapeutic agent.

62. The method of claim 61, wherein said another therapeutic agent is a chemotherapeutic agent.

63. The method of claim 62, wherein said chemotherapeutic agent is selected from the group consisting of doxorubicin, 5-fluorouracil (5 FU), cisplatin (CDDP), docetaxel, gemcitabine, pacietaxel, vinblastine, etoposide (VP-16), camptothecin, actinomycin-D, mitoxantrone and mitomycin C.

64. The method of claim 44, further comprising administering said complex in combination with radiation therapy.

65. The method of claim 64, wherein said radiation therapy is selected from the group consisting of gamma radiation, X-rays, UV irradiation, microwaves and electronic emissions.

66. The method of claim 61, wherein said another therapeutic agent is administered before said complex.

67. The method of claim 61, wherein said another therapeutic agent is administered subsequent to said complex.

68. The method of claim 64, wherein said radiation therapy is administered before said complex.

69. The method of claim 64, wherein said radiation therapy is administered subsequent to said complex.

70. The method of claim 44, wherein said mammal is a human.

* * * * *

SEQUENCE LISTING

```
<160> NUMBER OF SEQ ID NOS: 1

<210> SEQ ID NO 1
<211> LENGTH: 15
<212> TYPE: DNA
<213> ORGANISM: Artificial Sequence
<220> FEATURE:
<223> OTHER INFORMATION: HER-2 anti-sense oligonucleotide

<400> SEQUENCE: 1
tccatggtgc tcact                                                    15
```